(12) United States Patent
Schwartz et al.

(10) Patent No.: US 8,355,552 B2
(45) Date of Patent: Jan. 15, 2013

(54) AUTOMATED DETERMINATION OF LYMPH NODES IN SCANNED IMAGES

(75) Inventors: Lawrence H. Schwartz, New York, NY (US); Binsheng Zhao, Forest Hills, NY (US); Jiayong Yan, Roosevelt Island, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1043 days.

(21) Appl. No.: 12/142,766

(22) Filed: Jun. 19, 2008

(65) Prior Publication Data

US 2008/0317314 A1  Dec. 25, 2008

Related U.S. Application Data

(60) Provisional application No. 60/945,333, filed on Jun. 20, 2007.

(51) Int. Cl.
*G06K 9/00* (2006.01)
(52) U.S. Cl. ........................................ 382/131; 382/133
(58) Field of Classification Search .................. 382/128, 382/131, 133; 600/410
See application file for complete search history.

(56) References Cited

U.S. PATENT DOCUMENTS

| | | | |
|---|---|---|---|
| 7,203,354 B2 | 4/2007 | Wilson et al. | |
| 7,702,153 B2 | 4/2010 | Hong et al. | |
| 7,783,091 B2 | 8/2010 | Rinck et al. | |
| 7,813,536 B2 | 10/2010 | Ma et al. | |
| 2005/0201606 A1 | 9/2005 | Okada et al. | |
| 2006/0018548 A1 | 1/2006 | Chen et al. | |
| 2007/0081706 A1* | 4/2007 | Zhou et al. | 382/128 |
| 2008/0075345 A1 | 3/2008 | Unal et al. | |
| 2008/0171932 A1* | 7/2008 | Yan et al. | 600/410 |

(Continued)

FOREIGN PATENT DOCUMENTS

WO 2004088589 10/2004

(Continued)

OTHER PUBLICATIONS

W. Lu et al., Fast Free-form Deformable Registration via Calculus of Variations, Physics in Medicine and Biology, Jun. 28, 2004, pp. 3067-3087, vol. 49, No. PII: S0031-9155(04)7, Publisher: Institute of Physics Publishing, Published in: Bristol, United Kingdom.

(Continued)

*Primary Examiner* — Rochelle-Ann J Blackman
(74) *Attorney, Agent, or Firm* — Evans & Molinelli PLLC; Eugene J. Molinelli

(57) ABSTRACT

Techniques include automatically detecting a lymph node in a scanned image of a body without human intervention, using one or more of three approaches. First, a subset of scanned images is determined, which belongs to one anatomical domain. A search region for lymph tissue is in a particular spatial relationship outside an anatomical object in the domain. Second, scanned images are segmented without human intervention to determine a boundary of a particular lymph node. The scanned images and outline data are received. Some of these embodiments automatically segment by determining an external marker, based on the outline data, and an internal marker, based on a geometric center of the outline data or thresholds determined automatically inside detected edges, or both, for a marker-controlled watershed algorithm. Third, based on lymph node data at a particular time, a second scanned image at a different time is segmented automatically, without human intervention.

27 Claims, 16 Drawing Sheets

U.S. PATENT DOCUMENTS

| | | |
|---|---|---|
| 2010/0027865 A1 | 2/2010 | Wels et al. |
| 2011/0194742 A1 | 8/2011 | Buelow et al. |

FOREIGN PATENT DOCUMENTS

| | | |
|---|---|---|
| WO | 2005035061 | 4/2005 |
| WO | 2009074288 | 6/2009 |
| WO | 2012019162 | 2/2012 |

OTHER PUBLICATIONS

Luc Vincent, Morphological Grayscale Reconstruction in Image Analysis: Applications and Efficient Algorithms, Transactions on Image Processing, Apr. 2, 1993, pp. 176-201, vol. 2, No. 2, Publisher: IEEE, Published in: New York, NY.

J. Y. Yan et al, Lymph Node Segmentation from CT Images using Fast Marching Method, Computerized Medical Imaging and Graphics , Jan. 1, 2004, pp. 33-38, vol. 28, Publisher: Elsevier Ltd, Published in: Amsterdam, Netherlands.

J. Yan et al., Marker-controlled Watershed for Lymphoma Segmentation in Sequential CT Images, Med. Phys., Jul. 1, 2006, pp. 2452-2460, vol. 33, No. 7, Publisher: American Association of Physicists in Medicine , Published in: College Park, Maryland, US.

Yan et al., Automated Matching and Segmentation of Lymphoma on Serial CT Examinations, Medical Physics, Jan. 1, 2007, pp. 55-62, vol. 34, No. 1, Publisher: American Association of Physicists in Medicine , Published in: College Park, Maryland, USA.

S. G. Armato III et al, "The Reference Image Database to Evaluate Response to Therapy in Lung Cancer (RIDER) Project: A Resource for the Developm", "Clinical Pharmacology and Therapeutics", Oct. 2008, pp. 448-456, vol. 84, No. 4, Publisher: American Society for Clinical Pharmacology and Therapeutics, Published in: www.nature.com/cpt.

Tony F. Chan and Luminita A. Vese, "Active Contours Without Edges", "IEEE Transactions on Image Processing", Feb. 2001, pp. 266-277, vol. 10, No. 2, Publisher: IEEE, Published in: http://ieeexplore.ieee.org.

R. B. Dubey et al., "Semi-automatic Segmentation of MRI Brain Tumor", "ICGST-GVIP Journal", Aug. 2009, pp. 33-40, vol. 9, No. 4, Publisher: ICGST, Published in: www.icgst.com.

Shawn Lankton and Allen Tannenbaum, "Localizing Region-Based Active Contours", "IEEE Transactions on Image Processing", Nov. 2008, pp. 2029-2039, vol. 17, No. 11, Publisher: IEEE, Published in: http://ieeexplore.ieee.org.

G. McLennan et al., "Imaging as a Biomarker for Therapy Response: Cancer as a Prototype for the Creation of Research Resources", "Clinical Pharmacology and Therapeutics", Oct. 2008, pp. 433-436, vol. 84, No. 4, Publisher: Nature Publishing Group, Published in: www.nature.com/cpt.

Michael F. McNitt-Gray et al., "Computed Tomography Assessment of Response to Therapy: Tumor Volume Change Measurement, Truth Data, and Error", "Translational Oncology", Dec. 2009, pp. 216-222, vol. 2, No. 4, Publisher: Neoplasia Press, Inc., Published in: www.transonc.com.

P. David Mozley et al., "Measurement of Tumor Volumes Improves RECIST-Based Response Assessments in Advanced Lung Cancer", "Translational Oncology", Feb. 2012, pp. 19-25, vol. 5, No. 1, Publisher: Neoplasia Press, Inc. , Published in: www.transonc.com.

Binsheng Zhao et al., "Lung Cancer: Computerized Quantification of Tumor Response—Initial Results", "Radiology", Dec. 2006, pp. 892-898, vol. 241, No. 3, Publisher: Radiological Society of North America, Published in: http://radiology.rsna.org/content/241/3.toc.

* cited by examiner

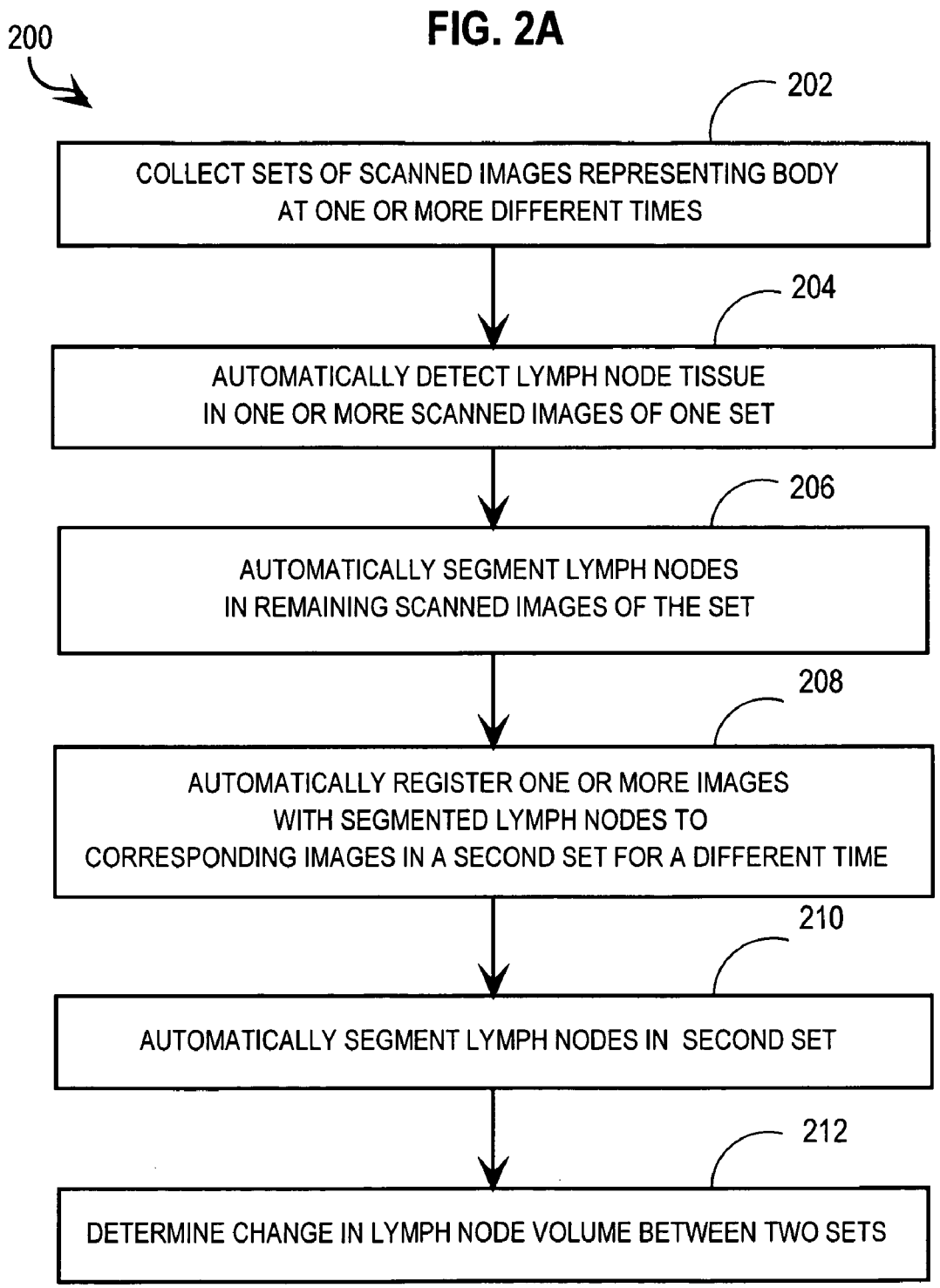

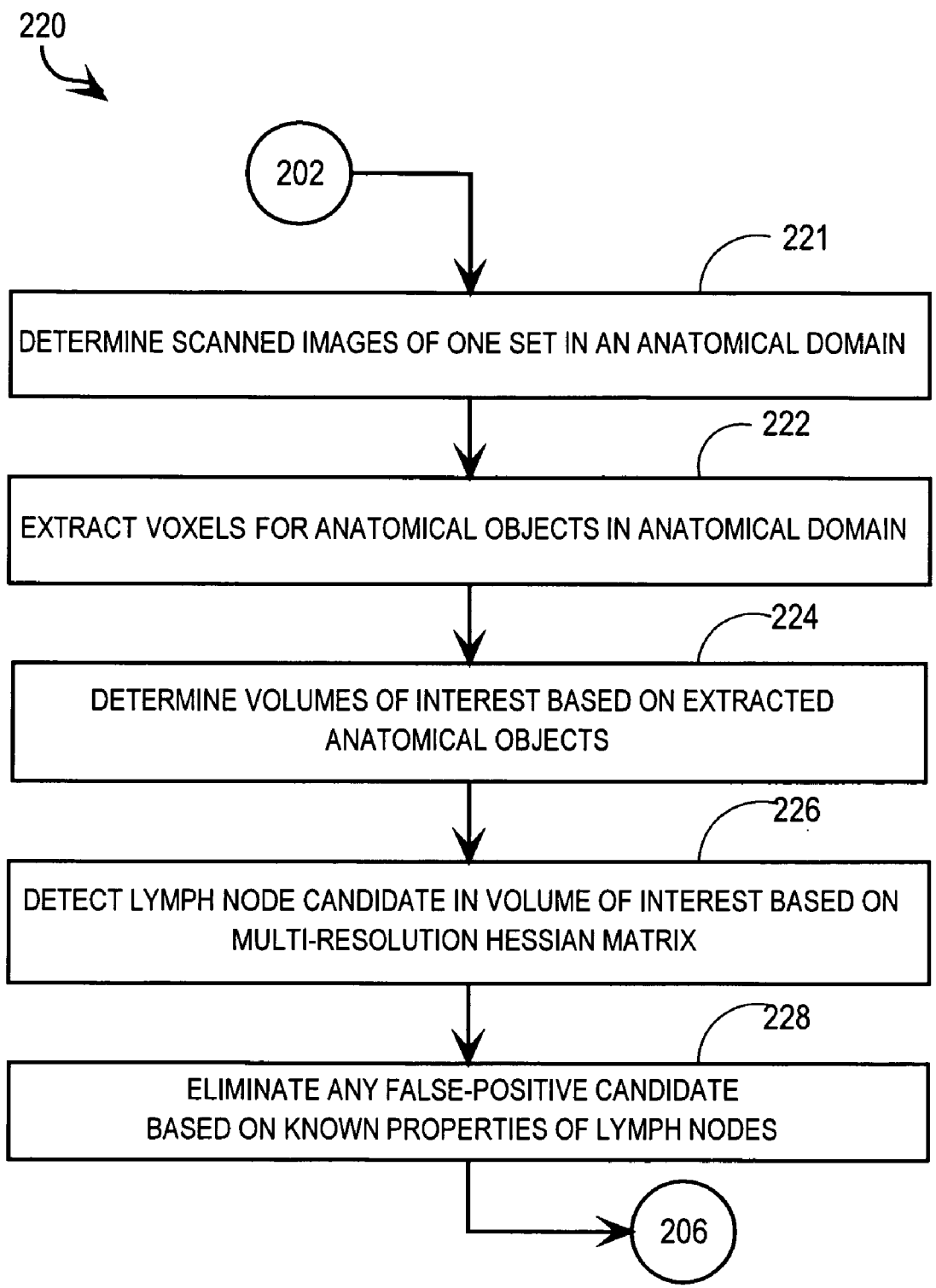

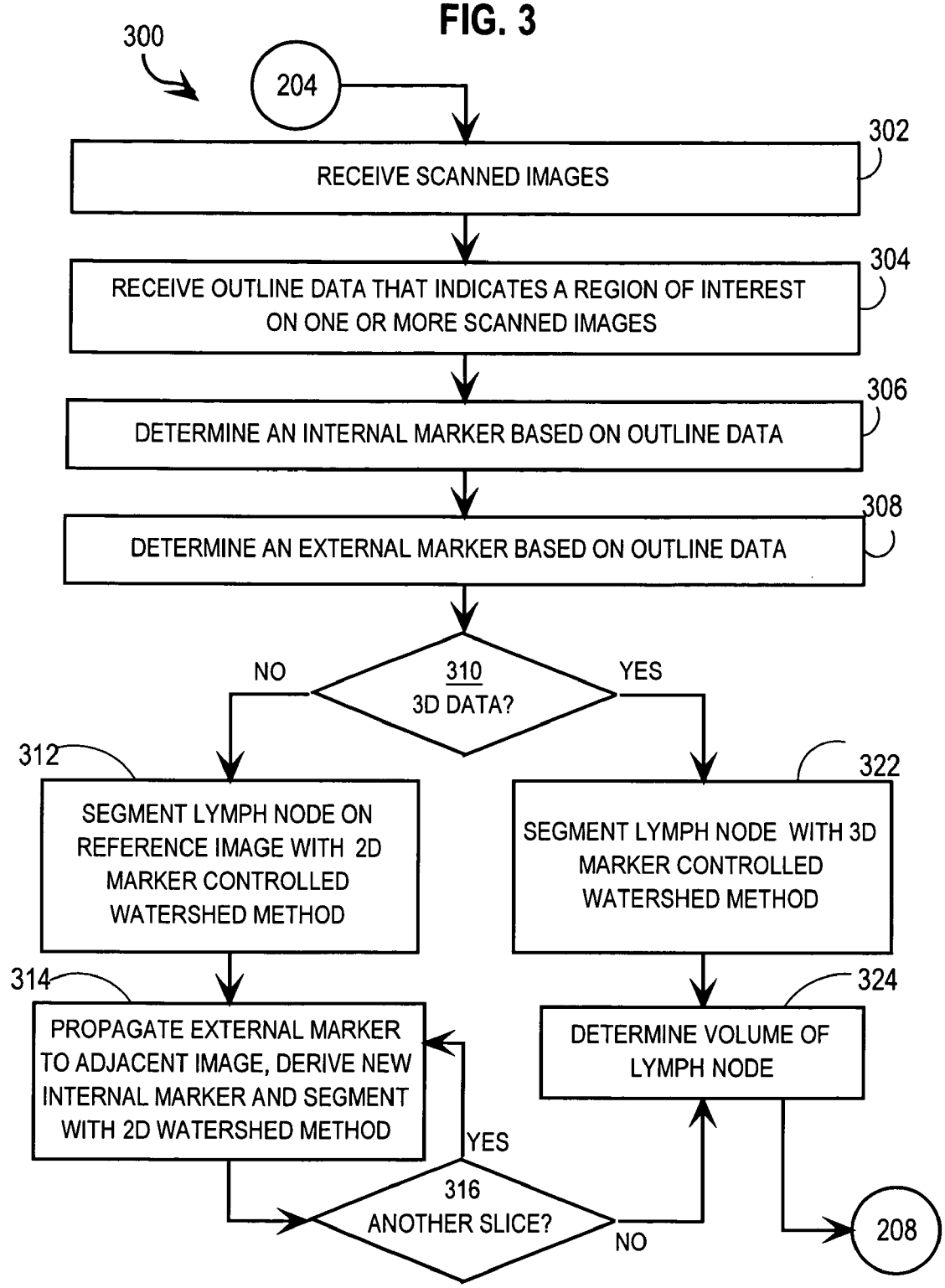

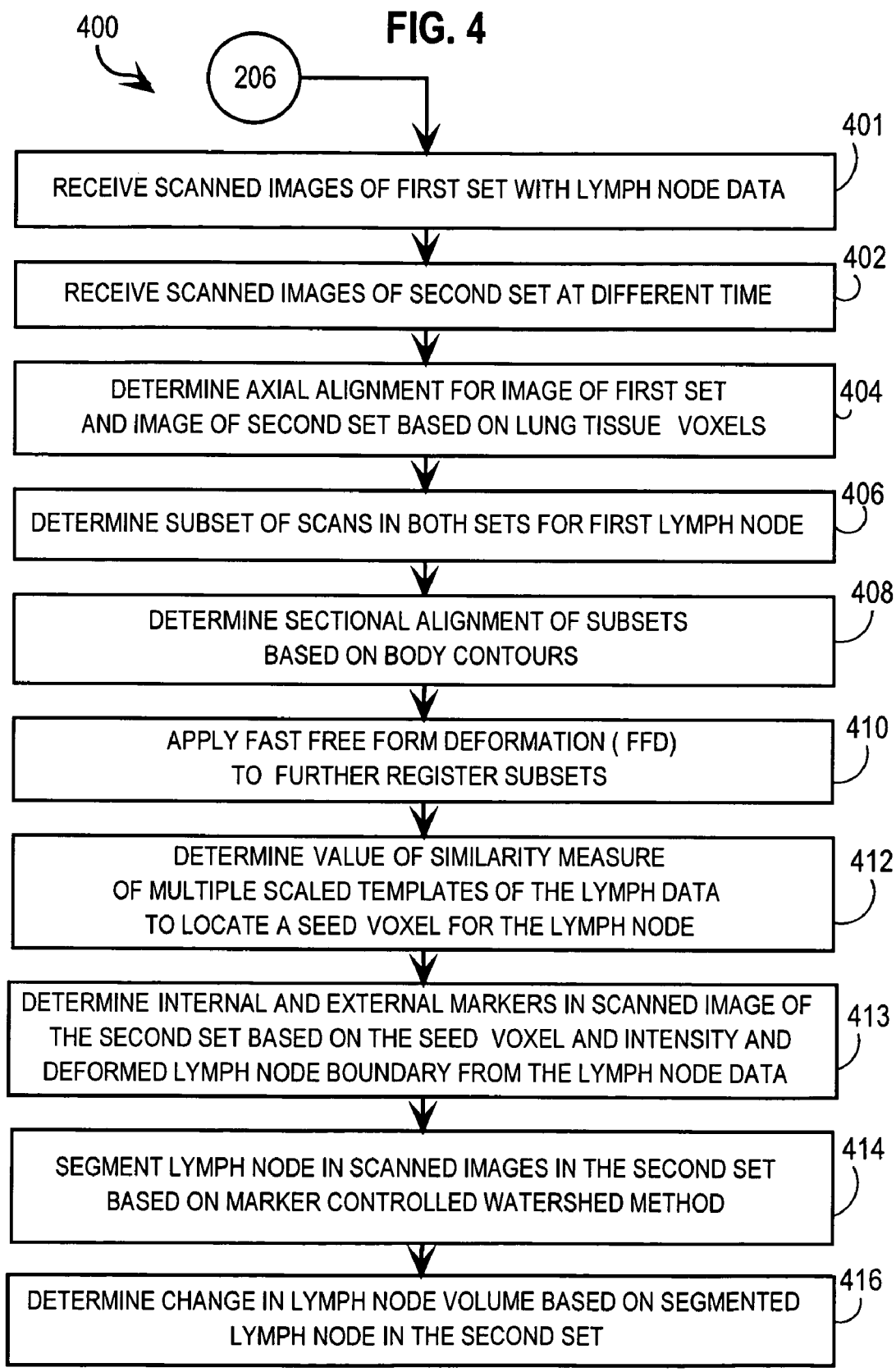

510
520
530

540

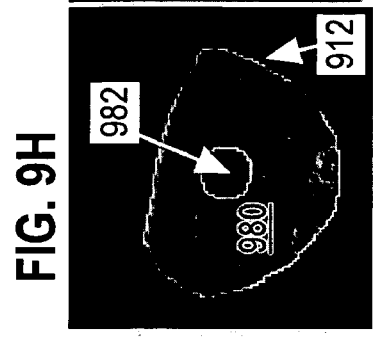
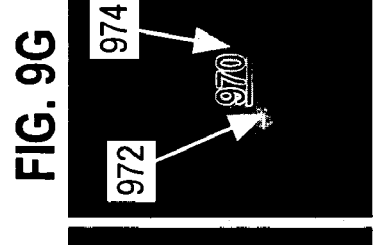
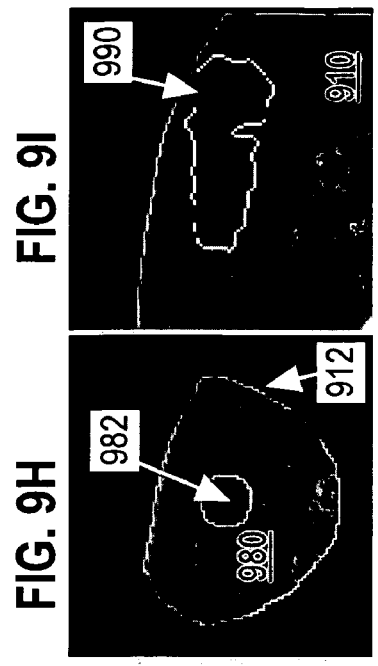
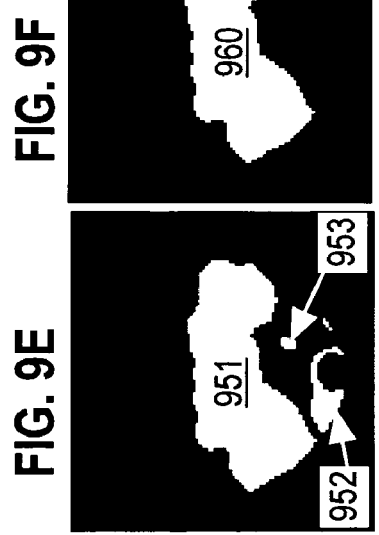
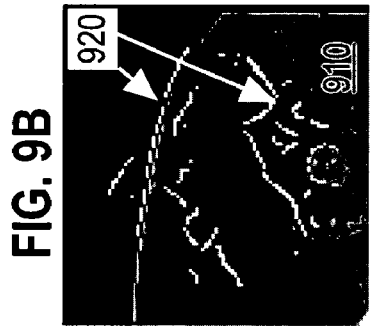
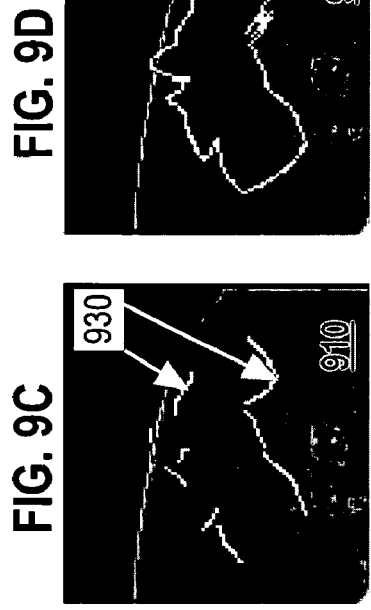
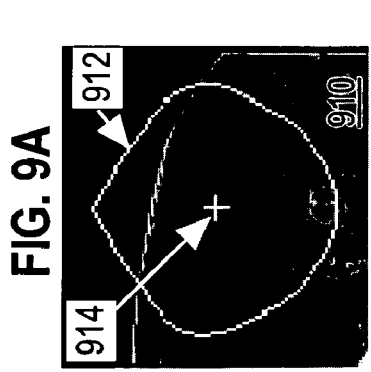

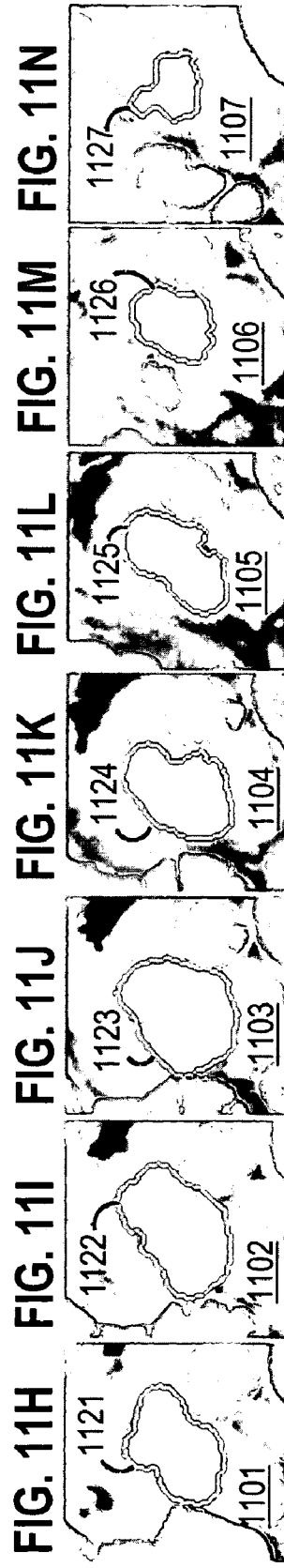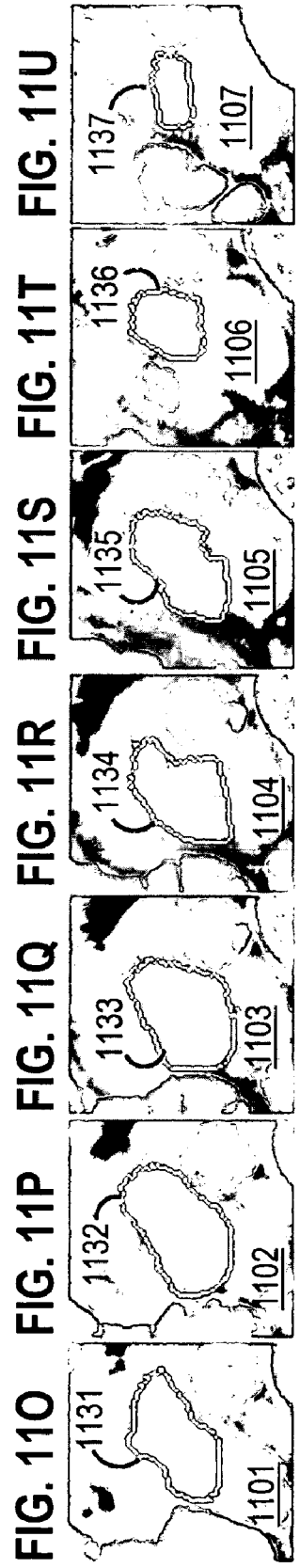

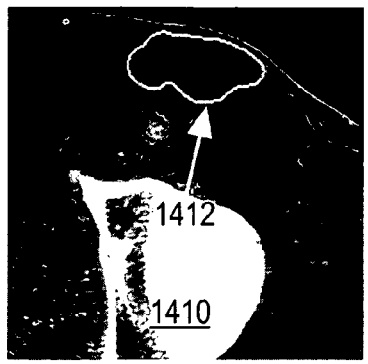 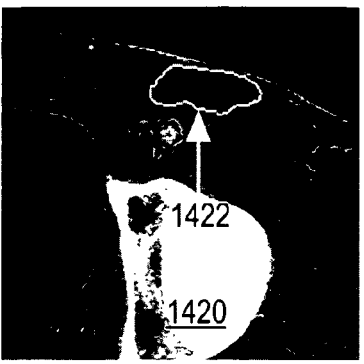 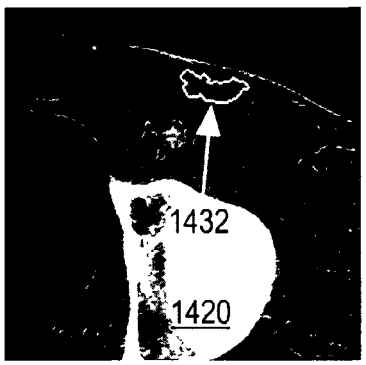
FIG. 14A    FIG. 14B    FIG. 14C
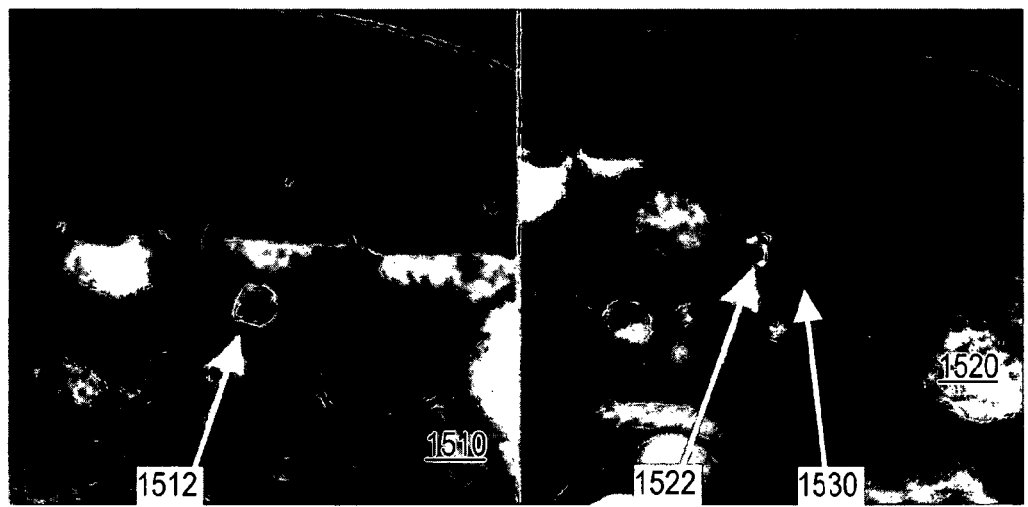
FIG. 15A    FIG. 15B

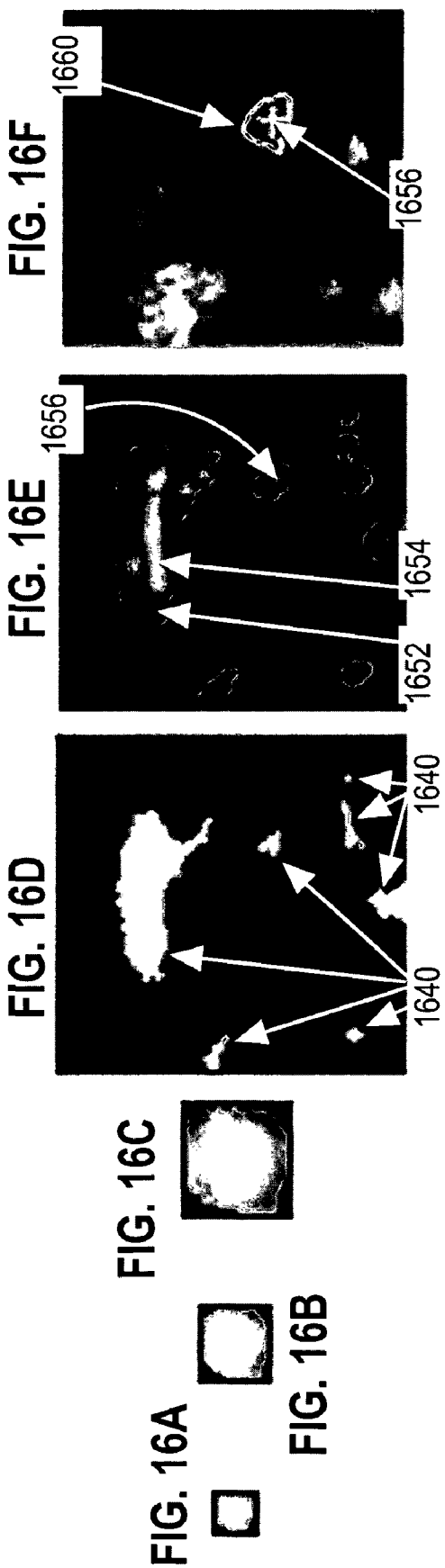

AUTOMATED DETERMINATION OF LYMPH NODES IN SCANNED IMAGES

CROSS-REFERENCE TO RELATED APPLICATIONS

This application claims benefit of Provisional Appln. No. 60/945,333, filed Jun. 20, 2007, the entire contents of which are hereby incorporated by reference as if fully set forth herein, under 35 U.S.C. §119(e).

BACKGROUND

1. Technical Field

The present disclosure relates generally to automated determination of lymph nodes in non-invasive scanned images of a body, such as in X-ray computed tomography (CT) scans and magnetic resonance imagery (MRI) scans of a human body.

2. Background

One way that tumors spread is through a patient's lymphatic system. Lymph node metastasis is a significant prognostic factor in many types of primary solid and hematologic malignancies. A patient's appropriate staging for either surgical or medical therapy depends upon the recognition and proper evaluation of lymph nodes throughout the body. A patient's disease prognosis also depends on the extent of lymph node involvement with a tumor at the time of diagnosis. After a patient has been treated with either surgery, radiation therapy or medical (chemotherapy) therapy, evaluation of these lymph nodes for decrease in size and number (response to therapy) or increase in size and number (progression or worsening of disease) is critical for judging the success or failure of a therapy and whether to continue with a successful therapy or change to a different therapy because of treatment failure. Determination of extent and size change of the lymph nodes on longitudinal CT scans obtained at different times during the course of a patient's active treatment and follow up after active treatment plays an important role throughout the practice of oncology.

The detection of lymph nodes, especially small lymph nodes, is difficult and tedious for a radiologist, because lymph nodes are "intertwined" with normal anatomic structures such as blood vessels and the bowel. Detection of these lymph nodes is critical for proper staging of a patient's tumor. If a lymph node is missed, i.e., not identified, a patient may be deemed mistakenly to have a local tumor which has not spread. This can result in inappropriate treatment for their cancer, for instance, by subjecting the patient to unnecessary surgery that would not have been performed if it had been recognized that the tumor had involved a lymph node. Identification of a structure as a lymph node which is not, could have similar dire consequences. For example, the patient can be deemed to have diffuse disease, for which surgery is not appropriate, when they may in fact have local disease for which surgery is the correct treatment. Lacking correct treatment, the patient's cancer may spread unnecessarily and threaten the patient's health and life.

Measurement of lymph nodes on medical imaging is one of the principal ways of determining if a lymph node may be involved with tumor. There are anatomically and pathologically defined cut off values for determining if a lymph node may have tumor in it or not. In general the larger a lymph node, the more suspicious it is for having tumor. The cut off values may be determined by individual lymph node region or group with an appropriately acceptable sensitivity and specificity. Evaluation of response to either a chemotherapy, surgery or radiation therapy is critical for determining if a treatment (either conventional or experimental) is efficient or if an experimental agent is effective against a specific tumor type.

For the past three decades, the standard way to assess response of tumors to therapy has been to use radiographic images, principally CT or magnetic resonance imaging (MRI), to measure tumor size using the bi-dimensional World Health Organization (WHO) criteria or uni-dimensional RECIST criteria. The bi-directional WHO criteria is based upon a temporal change in the sum of the target tumor size on multiple transverse images, in which tumor size on a transverse image is measured as the cross product of the two greatest perpendicular diameters. A transverse image is one that represents a body's internal tissues in a plane perpendicular to an axial direction; and the axial direction is parallel to the body's long axis, such as the direction from the top of a typical human body's head to the bottom of that body's feet. The uni-dimensional RECIST criteria is based upon a temporal change in the sum of the target tumor sizes on multiple transverse images, in which tumor size on a transverse image is measured by the tumor's maximum diameter.

However, the measurement of tumors on medical imaging is a manual and subjective task performed by a trained radiologist according to current clinical practice. Studies have shown significant variability in therapeutic response assessment. Reasons for the variability in response assessment include radiologists' intra- and inter-observer variability, imaging protocols (e.g., phase of intravenous contrast administration and image resolution) and measurement techniques used (e.g., hand-held caliper, electronic caliper, and semi-automated/automated technique. (See for example, Thiesse P, Ollivier L, Di Stefano-Louineau D, et al. "Response rate accuracy in oncology trials: Reasons for inter-observer variability," *J Clin Oncol.* 1997; vol. 15, pp 3507-3514.)

State-of-the-art medical imaging modalities in combination with advanced image processing algorithms are revolutionizing the traditional diagnostic methods in radiology and oncology. Older model CT scanners produced transverse plane images (called slices) with two dimensional picture elements (called pixels) at positions with substantial gaps in the axial direction, leading to partial volume artifacts, such as poor descriptions of axial edges. It is now technically feasible with multi-detector-row CT scanners to acquire images with isotropic three dimensional picture elements (called volume elements, or voxels) with sub-millimeter resolution along the perpendicular x, y directions in the transverse plane and in the axial (z) direction. Typically, the x direction is from the body's left side to the body's right side in the transverse plane; and, the y direction is from the body's back (posterior) to the body's front (anterior). This has reduced the partial volume artifacts associated with more traditional CT images; and true tumor volumes can now be measured with a high degree of accuracy. Asymmetric changes, particularly those along the axial direction, can be better detected with volumetric rather than with uni-dimensional or bi-dimensional measurements. The volumetric methods may help detect metastasis early and provide earlier and more accurate assessment of response to therapy.

While methods have been developed to assist the radiologist in finding tumors, to applicants' knowledge no methods are currently available that automatically determine lymph nodes in non-invasive scanned images without human intervention. This is because there are significant challenges in assessing multiple sites of lymph nodes throughout the body, and different surrounding structures with varying intensity contrasts to the lymph nodes.

Some investigators evaluated several standard techniques using images of phantoms and enhanced lymph nodes in rabbits (see, Rogowska J, Ketth B, Scott G G et al., "Evaluation of selected two-dimensional segmentation techniques for computed tomography quantization of lymph nodes," *Investigative Radiology*, 1996, vol. 31, pp 138-145, hereinafter Rogowska). Rogowska found that a Sobel/watershed technique and an interactive deformable contour algorithm had advantages over the other techniques with regard to user interaction, reproducibility and accuracy. However, results assume manual input of internal and external markers by a human to initialize the methods.

Others attempted to semi-automatically segment lymph nodes using a two-dimensional (2-D) and then a three-dimensional (3-D) active contour method. (See Honea D M, Ge Y, Snyder W E, et al., "Lymph node segmentation using active contours", *Proc. SPIE,* 1997, vol. 3034, pp 265-273; and Honea D M, and Snyder W E, "Three-Dimensional active surface approach to lymph node segmentation", *Proc. SPIE,* 1999; vol. 3661, pp 1003-1011, both referenced hereinafter as Honea). The Honea algorithms required well-defined edges and high similarity of the node boundaries between adjacent slices. These conditions can not be satisfied in may scanned images.

Based on region intensity features and a fast marching method, still others proposed an improved fast marching algorithm to segment lymph nodes. (See Yan J, Zhuang T, Zhao B, Schwartz L H, "Lymph node segmentation from CT images using fast marching method," *Computerized Medical Imaging and Graphics,* 2004, vol. 28, pp 33-38, hereinafter Yan.) The Yan algorithm was effective when the nodes had relatively homogenous intensities. However, the Yan results required a manually drawn initial circle to be as close as possible to the node boundary, a requirement which might not be satisfied when automatically segmenting sequential images.

Accordingly there is a need for an automated or semi-automated system that can objectively and accurately detect or measure lymph nodes or assess change in lymph node size on temporally separated CT scans in clinical practice, which does not suffer the disadvantages of prior art approaches.

SUMMARY OF THE INVENTION

Techniques are provided for detecting or segmenting lymph node scan elements in scanned images of the internal tissues of a body. As used herein after, the term scan element refers to a two dimensional (2D) or three dimensional (3D) spatial element for which an atomic value of intensity is available from a scanning device that non-invasively images internal tissues of a body. The term voxel is herein used as a convenient shorthand for scan element, and thus is to be understood to include either or both pixels and voxels, as appropriate in the context. Scanned images are also called scans herein for convenience, and represent tissue in a transverse plane also called a slice herein.

In a first set of embodiments, a method includes automatically detecting a lymph node in a scanned image of internal tissues of a body without human intervention. In some embodiments of this set, the method also includes receiving multiple scanned images representing corresponding different slices of the body between a neck of the body and a bottom of a pelvis of the body. A subset of the scanned images is determined, which belongs to one anatomical domain, such as a chest domain, an abdomen domain, or a pelvis domain. In some embodiments of this set, the method also includes determining voxels in the subset associated with an anatomical object that is not a lymph node and which is associated with the anatomical domain. Automatically detecting the lymph node then includes determining voxels in a search region of a particular scanned image of the subset in a particular spatial relationship outside the voxels associated with the anatomical object.

In another set of embodiments, a method includes receiving a set of one or more scanned images representing internal tissues of a body at a particular time and receiving outline data. The outline data indicates a region of interest in the set of one or more scanned images, which encloses voxels that represent a particular lymph node. The set of one or more scanned images is segmented without human intervention to identify a lymph node boundary between voxels that represent the lymph node and voxels that do not. In some embodiments of this set, the scanned images are automatically segmented by determining an external marker based on the outline data. An internal marker is determined based, at least in part, on a geometric center of the outline data. A marker-controlled watershed algorithm, which uses the external marker and the internal marker, is applied to determine the lymph node boundary. In some embodiments, the internal marker is also based on detected edges and dual thresholds automatically determined inside the detected edges.

In another set of embodiments, a method includes receiving a first scanned image representing internal tissues of a body at a particular time, and lymph node data, and scanned images representing internal tissues of the same body at a different time. The lymph node data indicates a first set of voxels that represent tissue within a particular lymph node in the first scanned image. A second scanned image at the different time is segmented automatically, without human intervention, based on the lymph node data, to identify in the second scanned image a second set of voxels that represent tissue within a lymph node at the different time, which corresponds to the particular lymph node. In some embodiments of this set, first scanned image is received as part of particular scanned images at the particular time; and the lymph node data indicates the particular lymph node in a first subset of multiple scanned images from the particular scanned images. A second subset of images from the scanned images at the different time is determined, which includes the particular lymph node at the different time based on the lymph node data. In some of these embodiments, a geometric center of a body surface in the second subset is aligned with a geometric center of a body surface in the first subset. In some of these embodiments, the first subset is registered to the second subset with a non-rigid fast free form deformation (FFD) registration algorithm. The voxels of the particular lymph node after registering determine a search region in the second scanned image; and an initial set of lymph node voxels is determined based, at least in part, on the voxels in the search region.

In other embodiments, an apparatus, or logic encoded in one or more tangible media, or instructions encoded on one or more computer-readable media is configured to perform one or more steps of the above methods.

BRIEF DESCRIPTION OF THE DRAWINGS

The present disclosure is illustrated by way of example, and not by way of limitation, in the figures of the accompanying drawings and in which like reference numerals refer to similar elements and in which:

FIG. 2A is a flow diagram that illustrates at a high level a method for automatically detecting changes in lymph node volume over time, according to an embodiment;

FIG. 2B is a flow diagram that illustrates at a high level a method for performing a step of the method of FIG. 2A, according to an embodiment;

FIG. 3 is a flow diagram that illustrates at a high level a method for performing another step of the method of FIG. 2A, according to an embodiment;

FIG. 4 is a flow diagram that illustrates at a high level a method for performing two steps of the method of FIG. 2A, according to an embodiment;

FIGS. 9A through 9I are images that illustrate images and edges derived from a single CT scanned image and outline data, according to an embodiment;

FIGS. 11A through 11G are images that illustrate CT scanned images at seven axial locations, respectively, of an anatomical domain with outline data for CT scanned image 11C superimposed, according to an embodiment;

FIGS. 11H through 11N are images that illustrate CT scanned images of FIGS. 11A through 11G, respectively, with automatically segmented lymph node edges superimposed, according to an embodiment;

FIGS. 11O through 11U are images that illustrate CT scanned images of FIGS. 11A through 11G, respectively, with manual lymph node edges superimposed;

FIGS. 2A through 12G are renderings that illustrate simulated joined anatomical objects before or after detachment, according to an embodiment;

FIG. 14A is an image that illustrates a CT scanned image from a particular time with a detected boundary of a lymph node superimposed, according to an embodiment;

FIG. 14B is an image that illustrates a corresponding CT scanned image from a different time with, superimposed, the boundary of FIG. 14A deformed based on registration of the corresponding images, according to an embodiment;

FIG. 14C is an image that illustrates the corresponding CT scanned image of FIG. 14B with a newly determined lymph node boundary, according to an embodiment;

FIG. 15A is an image that illustrates a different CT scanned image from a particular time with a detected boundary of a lymph node superimposed, according to an embodiment;

FIG. 15B is an image that illustrates a corresponding CT scanned image from a different time with superimposed, the boundary of FIG. 15A deformed based on FFD registration of the corresponding images, according to an embodiment;

FIGS. 16A through 16C are images that illustrate templates at different scales based on a single lymph node, according to an embodiment;

FIGS. 16D through 16F are images that illustrate images and edges derived from a single CT scanned image at a different time and the templates of FIGS. 6A through 16C, according to an embodiment.

DESCRIPTION OF EXAMPLE EMBODIMENTS

A method and apparatus are described for automatically detecting or segmenting lymph nodes, or both, in non-invasive scanned images of a body. In the following description, for the purposes of explanation, numerous specific details are set forth in order to provide a thorough understanding of the present disclosure. It will be apparent, however, to one skilled in the art that an embodiment may be practiced without these specific details. In other instances, well-known structures and devices are shown in block diagram form in order to avoid unnecessarily obscuring the present disclosure.

Some embodiments are described in the context of lymph nodes in CT scanned images of a human body. However, the invention is not limited to this context. In other embodiments lymph nodes or spatially related anatomical objects, such as the aorta, liver and inferior vena cava, are detected or segmented in scans of human or animal bodies using any scanning device, such as CT scanners, MRI scanners, PET scanners, and multi-spectral X-ray scanners among others. In some embodiments, solid tumors with relatively homogeneous intensities in scanned images are detected or segmented or both, such as tumors of the lung, colorectal cancer, breast cancer, ovarian cancer, melanoma and kidney cancer.

1.0 Overview

Figure 1A:
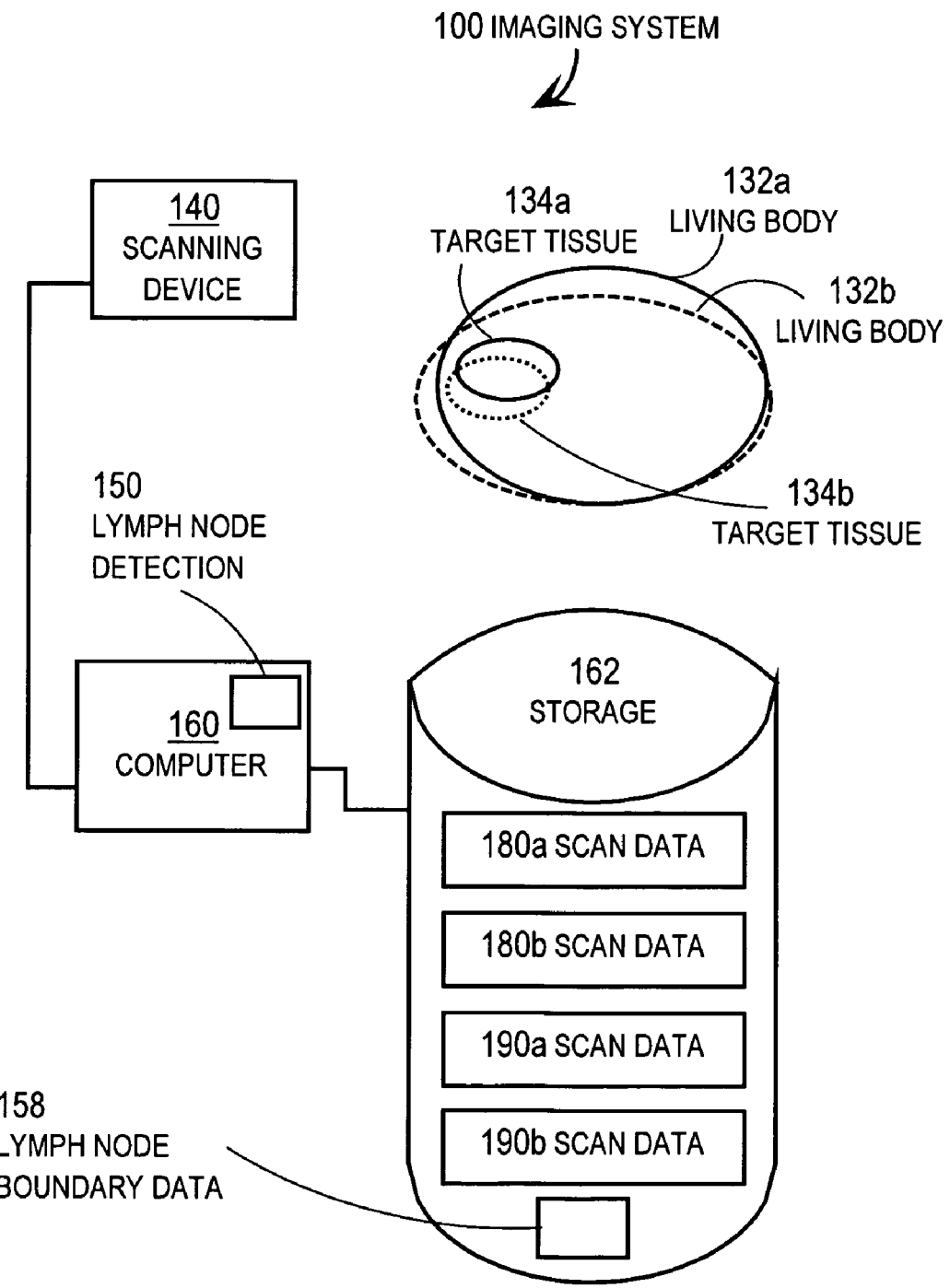
FIG. 1A is a block diagram that illustrates an imaging system for lymph nodes, according to an embodiment.

FIG. 1 is a block diagram that illustrates an imaging system 100 for lymph nodes, according to an embodiment.

The system 100 is designed for determining the spatial arrangement of soft target tissue in a living body. For purposes of illustration a living body is depicted, but is not part of the system 100. In the illustrated embodiment a living body is depicted in a first spatial arrangement 132a at one time and includes a target tissue in a corresponding spatial arrangement 134a. At a different time, the same living body is in a second spatial arrangement 132b that includes the same target tissue in a different corresponding spatial arrangement 134b.

In the illustrated embodiment, system 100 includes a scanning device 140, such as a full dose X-ray computed tomography (CT) scanner, or a magnetic resonance imaging (MRI) scanner. In some embodiments, the scanning device 140 is used at two or more different times. The device 140 is configured to produce scanned images that each represent a cross section of the living body at one of multiple cross sectional (transverse) slices arranged along the axial direction of the body, which is oriented in the long dimension of the body.

In system 100, data from the imager 140 is received at a computer 160 and stored on storage device 162. Computer systems and storage devices like 160, 162, respectively, are described in more detail in a later section. Scan data 180a, 180b, 190a, 190b based on data measured at imager 140 at two different times are stored on storage device 162. For example, scan data 180a and scan data 180b, which include scanned images at two slices separated in the axial direction, is stored based on measurements from scanning device 140 at one time. Scan data 190a, 190b, which include scanned images at two slices separated in the axial direction, is stored based on measurements from scanning device 140 at a different time.

In various embodiments, a lymph node detection process 150 operates on computer 160 to determine a boundary between scan elements of scan data which are inside and outside a lymph node. The boundary data is stored in lymph node boundary data 158 in associations with the scan data, e.g., scan data 180a, 180b, 190a, 190b.

Although system 100 is depicted with a particular number of scanning devices 140, computers 160, and scan data 150, 160 on storage device 162 for purposes of illustration; in other embodiments more or fewer scanning devices, computers, storage devices and scan data constitute an imaging system for determining spatial arrangement of lymph nodes.

Figure 1B:
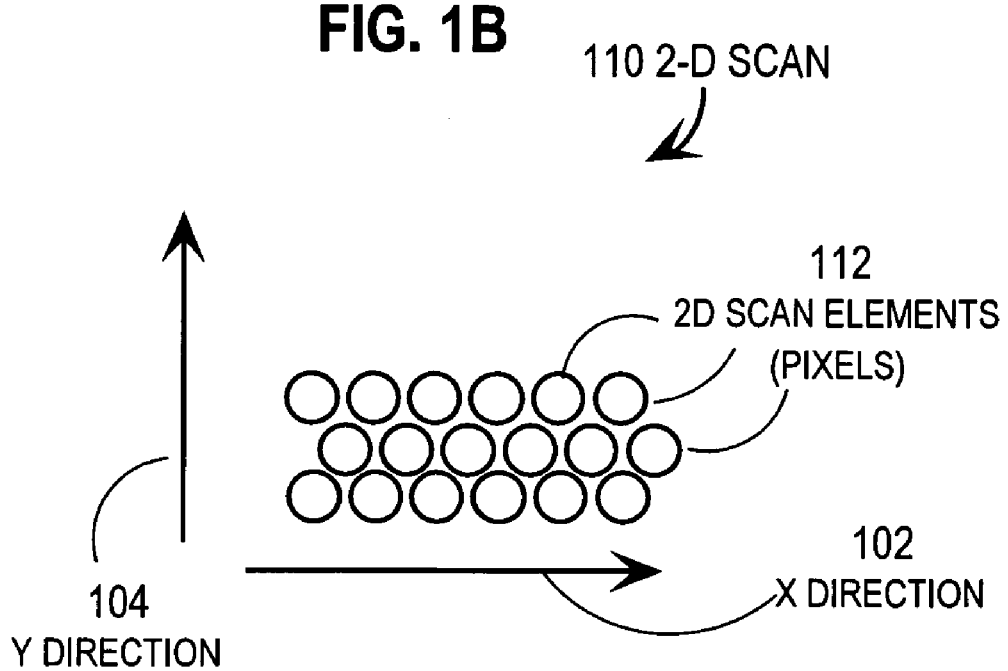
FIG. 1B is a block diagram that illustrates scan elements in a 2D scan.

FIG. 1B is a block diagram that illustrates scan elements in a 2D scan 110, such as one scanned image from a CT scanner. The two dimensions of the scan 110 are represented by the x direction arrow 102 and the y direction arrow 104. The scan 110 consists of a two dimensional array of 2D scan elements (pixels) 112 each with an associated position. Typically, a 2D scan element position is given by a row number in the x direction and a column number in the y direction of a rectangular array of scan elements. A value at each scan element position represents a measured or computed intensity that represents a physical property (e.g., X-ray absorption, or resonance frequency of an MRI scanner) at a corresponding position in at least a portion of the spatial arrangement 132a, 132b of the living body. Although a particular number and arrangement of equal sized circular scan elements 112 are shown for purposes of illustration, in other embodiments, more elements in the same or different arrangement with the same or different sizes and shapes are included in a 2D scan.

Figure 1C:
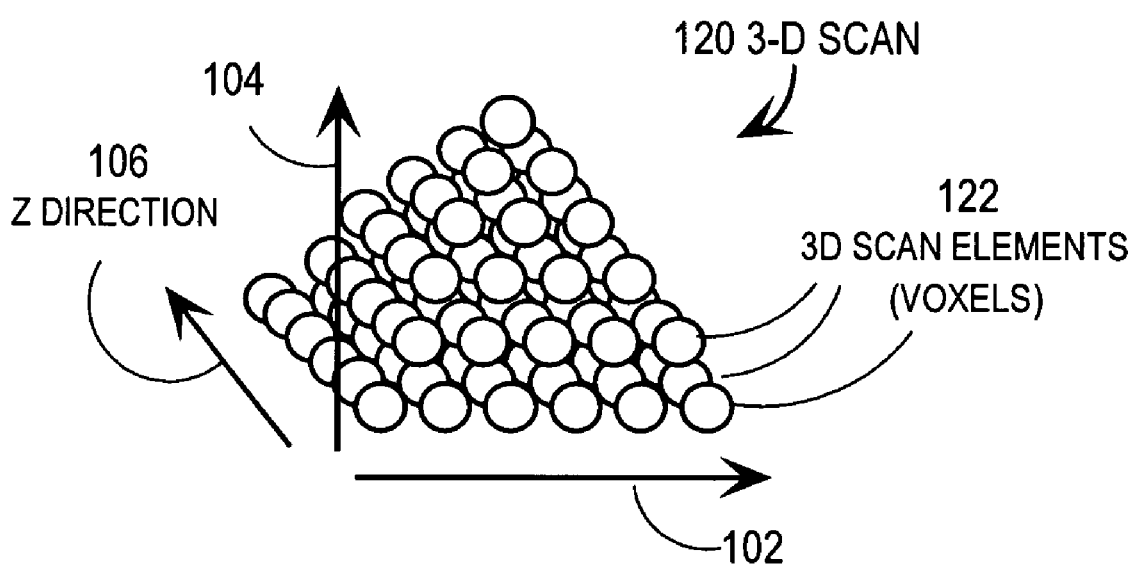
FIG. 1C is a block diagram that illustrates scan elements in a 3D scan.

FIG. 1C is a block diagram that illustrates scan elements in a 3D scan 120, such as stacked multiple scanned images from a CT imager or true 3D scan elements from volumetric CT imagers. The three dimensions of the scan are represented by the x direction arrow 102, the y direction arrow 104, and the z direction arrow 106. The scan 120 consists of a three dimensional array of 3D scan elements (also called volume elements and abbreviated as voxels) 122 each with an associated position. Typically, a 3D scan element position is given by a row number in the x direction, column number in the y direction and a scanned image number (also called a scan number) in the z (axial) direction of a cubic array of scan elements. A value at each scan element position represents a measured or computed intensity that represents a physical property (e.g., X-ray absorption for a CT scanner, or resonance frequency of an MRI scanner) at a corresponding position in at least a portion of the spatial arrangement 132a, 132b of the living body. Although a particular number and arrangement of equal sized spherical scan elements 122 are shown for purposes of illustration, in other embodiments, more elements in the same or different arrangement with the same or different sizes and shapes are included in a 3D scan.

The term voxels is used herein to represent both 2D scan elements (pixels) or 3D scan elements (voxels), or both, depending on the context.

3.0 Method

FIG. 2A is a flow diagram that illustrates at a high level a method 200 for automatically detecting changes in lymph node volume over time, according to an embodiment. Although steps in FIG. 2A and subsequent flow charts, FIG. 2B, FIG. 3 and FIG. 4, are shown in a particular order for purposes of illustration, in other embodiments, one or more steps may be performed in a different order or overlapping in time, in series or in parallel, or one or more steps may be omitted or added, or changed in some combination of ways.

In step 202, one or more sets of scanned images are collected. Each set includes one or more scanned images that represent the internal tissues of a body at a single time. The data may be collected in any manner known in the art. For example, in some embodiments, step 202 is performed by positioning the living body in range of scanning device 140 and operating the scanning device 140 to make measurements that are converted to stored scan data 180, 190 in storage unit 162. For example, volumetric CT images of the body are acquired helically using a standard clinical protocol and the image data is transferred to and stored on a standard local computer for further processing. Suitable scanners for obtaining the images include High-Speed CT series and LightSpeed CT series from General Electric Company, GE Healthcare of Piscataway, N.J. The image data can be transferred via a network and the computer can be any computer, e.g., a personal computer or a UNIX machine. In some embodiments, step 202 is performed by receiving the scan data 180 or 190 or both at computer 160 from storage device 162.

Any method may be used to receive this data. For example, in various embodiments, the data is included as a default value in software instructions, is received as manual input from a human operator on the local or a remote node, is retrieved from a local file or database, or is sent from a different node on the network, either in response to a query or unsolicited, or the data is received using some combination of these methods.

In step 204, tissue in one or more lymph nodes is detected automatically in one or more scanned images of one set (representing one or more slices of the body at one time). As used herein, detected lymph node tissue is designated by any of several means, including: 1] classifying individual voxels as representing lymph node tissue, 2] classifying individual voxels as representing tissue that belongs to a particular lymph node, 4] listing positions of a curve or surface that represents a boundary between lymph node tissue and different tissue in the body; and 4] listing positions of a curve or surface that represents a boundary between lymph node tissue of a particular lymph node and different tissue in the body. As used herein, segmenting lymph nodes means determining a 2D or 3D boundary between a particular lymph node and other tissue in the body.

Any method may be used to automatically detect lymph node tissues in one or more scans of the set. In an illustrated embodiment, the voxels that represent lymph node are determined using a method described in more detail below with reference to FIG. 2B. In some embodiments, a boundary of the voxels that represent lymph nodes in a first scanned image, or an outline enclosing a particular lymph node in that first image, is provided manually and step 204 is omitted.

In step 206, individual lymph nodes are segmented in the first set. In some embodiments, the step 206 includes using the detected lymph node tissue from step 204, or provided manually, to create an outline of a region of interest for producing a refined segmentation of lymph nodes. In some embodiments, the lymph node is segmented across multiple scanned images in the first set. Any method may be used to automatically segment the lymph nodes. In an illustrated embodiment, the segmented lymph node is determined using a marker-controlled watershed transformation algorithm described in more detail below with reference to FIG. 3. In some embodiments, a boundary of the voxels that represent a particular lymph node in the first set, is provided manually and step 206 is omitted.

In step 208, one or more images in the first set, with detected or segmented lymph nodes, are automatically registered to corresponding images in a second set for a different time. Any method may be used to perform this registration. In an illustrated embodiment, the registration is performed using a method described in more detail below with reference to FIG. 4.

In step 210, one or more images in the second set for the different time are segmented based on the registration determined in step 208 and the segmented or detected lymph nodes in the first set. Any method may be used to perform this segmentation. In an illustrated embodiment, the segmentation is performed using a method described in more detail below with reference to FIG. 4.

In step 212, a change in lymph node volume is determined automatically based on the segmented lymph nodes in the first set (determined in step 206) and the second set (determined in step 210). Any method may be used to determine the change in volume, including the WHO criteria and the RECIST criteria, among others.

In some embodiments, the detection of voxels representing lymph node tissue performed in step 204 is sufficient, and step 206 and following steps are omitted. In some embodiments, the segmentation of lymph nodes performed in step 206 is sufficient, and step 208 and following steps are omitted. In some embodiments, the segmentation of lymph nodes performed in step 210 is sufficient, and step 212 is omitted.

3.1 Automatic Detection of Lymph Node Tissue.

FIG. 2B is a flow diagram that illustrates at a high level a method 220 for performing a step of the method of FIG. 2A, according to an embodiment. Method 220 is directed to detecting lymph node tissue in scanned images based on spatial relationships to other anatomical objects evident in the scans and relevant to lymph node location. Such relevant anatomical objects are called landmarks-of-interest hereinafter; and, are identified on multiple scans of one set of scanned images. The anatomical objects that can be found in scanned images depend on the portion of the body the slice transects. Thus according to an illustrated embodiment, the set of scanned images is divided into two or more subsets of scanned images, where each subset represents a different anatomical domain.

3.1.1 Automatic Detection of Anatomical Domains.

In the illustrated embodiment, three anatomical domains are used to locate anatomical objects associated with lymph nodes between the neck of the body and the bottom of the pelvis of the body. The first anatomical domain is the chest and extends from the first scanned image closest to the neck of the body and extends to include all slices that show lung tissue. The second anatomical domain is the abdomen that extends from below the chest to the top of the hip (ilium). The ilium is evident in a profile of bone tissue area among the scanned images, as described in more detail below. The third anatomical domain is the pelvis that extends from the top of the ilium to the last scan at the bottom of the pelvis.

Because of the locations of the lymph node clusters, anatomic landmarks-of-interest are different in the three domains and involve different techniques to detect and extract. As the term is used herein, an object is extracted from a set of images when the voxels that make up that object are labeled to indicate that object. In some embodiments, the voxels of the extracted object are removed from the image, effectively being given an intensity value of zero.

In the chest domain, the aorta and trachea are the landmarks. In the abdomen domain, almost all normal organs/tissues are extracted to identify lymph nodes and to reduce false-positives. In the pelvis domain, the aorta and external arteries are the landmarks. To reduce false-positive rate, other organs/tissues, including the liver, stomach, spleen, kidney, bladder, intestines, inferior vena cava, psoas and muscles in abdomen and pelvis anatomical domains, are approximately extracted from the images. The detection and extraction of each of the anatomic landmarks and relevant organs/tissues for CT scanned images are illustrated in more detail below.

In step 221, one or more subsets of the scanned images in the first set are selected. Each subset includes all scanned images that belong to a particular anatomical domain.

In an illustrated embodiment, step 221 includes determining a first subset of scanned images for the chest anatomical domain, a second subset of scanned images for the abdominal anatomical domain, and a third subset of scanned images for the pelvis anatomical domain. In most scanned images, boney material and lung tissue are most easily identified and extracted. And the domains of the illustrated embodiment are based on the detection of these tissues.

For example, in step 221 bone voxels are determined in volumetric CT images. Any method known in the art may be used to identify and extract boney structures. For example, in the illustrated embodiment, voxels are identified, which have intensity values that exceed a high bone threshold value, e.g., greater than about 160 Hounsfield units (HU) in CT images. A group of geometrically contiguous voxels with similar intensity values is called a component or an object. All 3D objects having intensity values higher than the threshold value are determined as bone-like objects. The largest 3D object is classified as a major bony structure and is extracted from the images. The minimum size (e.g., as indicated by the number of voxels in the group, or volume in cubic millimeters, mm, 1 mm=$10^{-3}$ meters) for a major boney structure can be determined readily by one of ordinary skill in the art. The area of bone structures on each scanned image is also determined, e.g., in number of voxels or number of square millimeters, for constructing a bone area profile, as described in more detail below.

In the illustrated embodiment, the lung objects are also determined. Any method may be used. In an illustrated embodiment, the lung objects are automatically defined in a set of CT images as described by Shiying Hu, Eric A. Hoffman and Joseph M. Reinhardt, "Automatic lung segmentation for accurate quantitation of volumetric X-ray CT images", *IEEE Transactions on Medical Imaging*, 2001, vol. 20, No. 6, pp. 490-498 (hereinafter, Hu), the entire contents of which are hereby incorporated by reference, except where terms are defined to be inconsistent with the use of those terms herein.

With the automatically extracted lungs and bony structures, the above-mentioned three sites can be automatically identified and separated along the axial direction. The chest starts from the lung apex and ends at the bottom of the lungs, which can be easily determined with the segmented lung tissues. The abdomen starts from the bottom of the lungs and ends at the top of the ilium. The pelvis starts from the top of the ilium and ends at the last image farthest from the neck. The top of the ilium is determined by analysis of a bone area profile.

Figure 6:
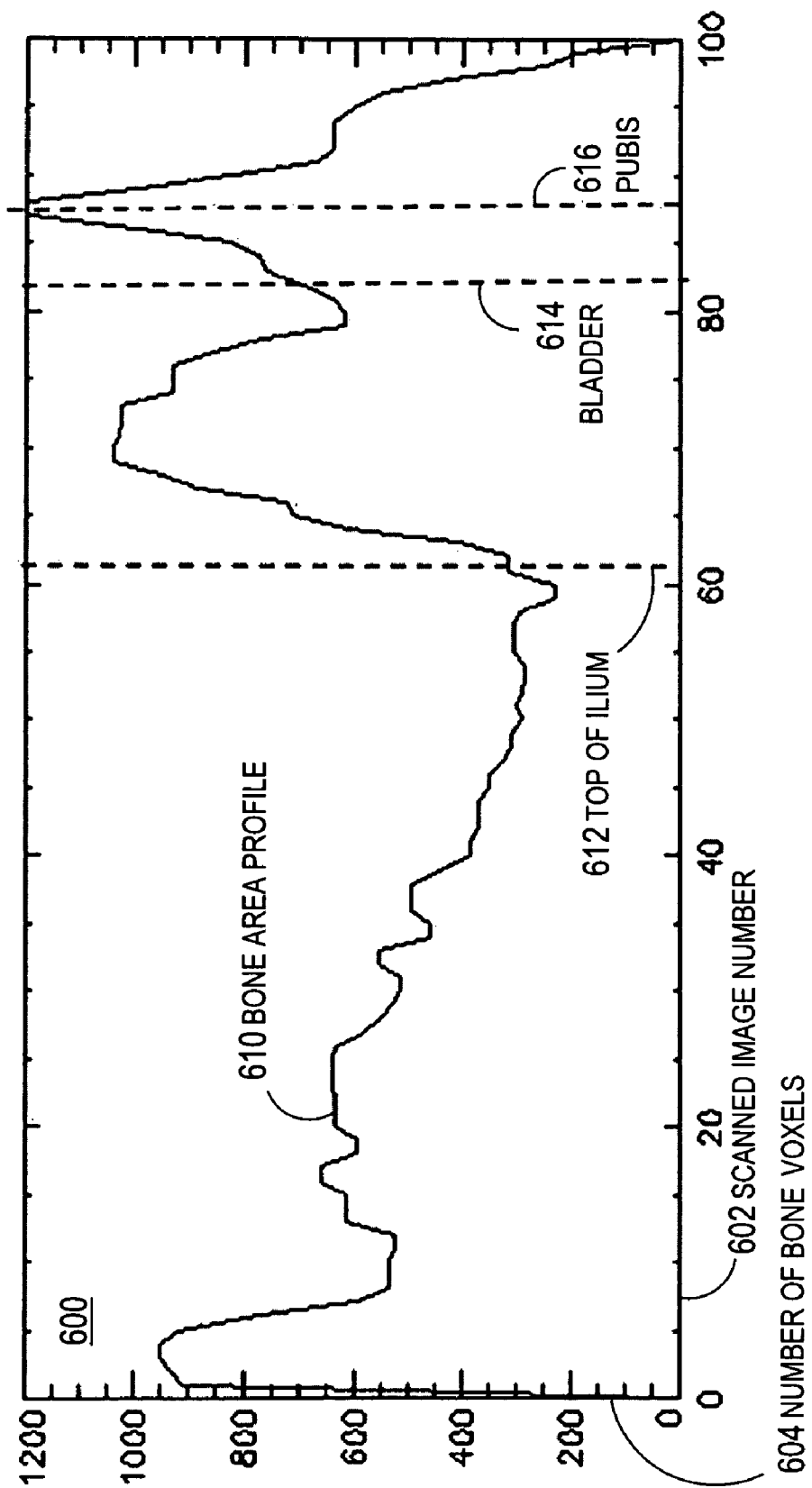
FIG. 6 is a graph that illustrates an anatomical domain based on a bone area profile derived from CT imagery, according to an embodiment.

FIG. 6 is a graph 600 that illustrates an anatomical domain based on a bone area profile derived from CT imagery, according to an embodiment. The horizontal axis 602 indicates the axial position in terms of scanned image number increasing from 1 for the scanned image closest to the neck to 100 for the scanned image at the bottom of the pelvis. The vertical axis 604 indicates the area of bone on each scanned image (e.g., expressed in number of voxels in a bone group). The bone area profile 610 shows a gradual decline through the chest to a broad minimum between about scanned image 40 to about scanned image 60, and two peaks between images 60 and 100. From the bone area profile, the axial position 612 of the image at the top of the ilium is selected. The image that has the fewest bones between the image containing the lung bottom and the image that has the most bones is considered as the location of the top of the ilium. Also shown in FIG. 6 is the axial position 616 of the pubis and the axial position 614 of the bladder. Thus, in the illustrated embodiment, the pelvis anatomical domain extends from image 61 to image 100.

3.1.2 Automatic Detection of Landmarks-of-Interest in the Chest Domain.

In step 222, voxels associated with the landmarks-of-interest are determined for each anatomical domain. Any method known in the art may be used.

In the chest anatomical domain, the anatomical landmarks-of-interest are the aorta and the trachea.

Trachea.

In CT images, voxels associated with the trachea are determined as described here. Voxels from the lung tissue with intensity values below a trachea threshold value of about −824 HU are determined. 3D objects are determined based on these voxels. The largest 3D object in the location between the right and left lungs is selected as the trachea, and its voxels are so labeled.

Figure 5A:
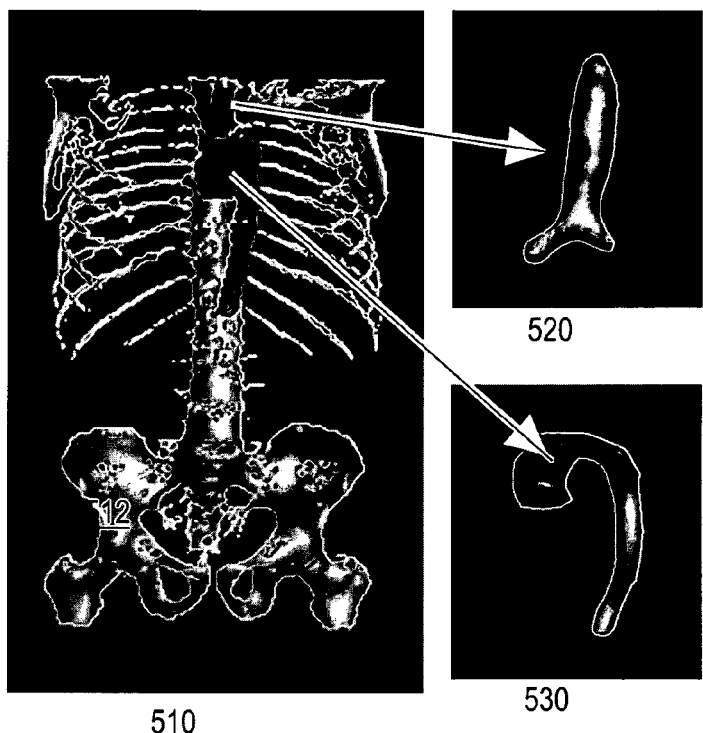
FIG. 5A is a block diagram that illustrates a relationship between three perspective renderings of anatomical objects extracted from CT imagery, according to an embodiment.
Figure 5B:
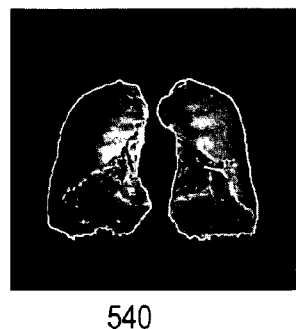
FIG. 5B is a perspective rendering that illustrates lung tissue extracted from CT imagery, according to an embodiment.

FIG. 5A is a block diagram that illustrates a relationship between three perspective renderings of anatomical objects extracted from CT imagery, according to an embodiment. Perspective surface rendering 510 illustrates lit surfaces of major bones, a trachea and an aorta extracted from CT images in a first set. The surface of trachea in rendering 510 is presented alone in perspective surface rendering 520; and the surface of aorta in rendering 510 is presented alone in perspective surface rendering 530, as indicated by arrows connecting the renderings. FIG. 5B is a perspective rendering that illustrates lung tissue extracted from CT imagery, according to an embodiment.

The voxels of the trachea are determined from the lung tissue rendered in FIG. 5B, using the method described above; and these voxels are labeled trachea voxels, e.g., by associating a trachea code value with the index or position of each voxel in the object. As described above, an object is extracted from a set of images when the voxels that make up that object are labeled to indicate that object. In some embodiments, the voxels of the extracted object are removed from the image, effectively being given an intensity value of zero.

Aorta.

Based on the extracted trachea and anatomic knowledge, the voxels of the ascending/descending aorta in the chest is determined. An aorta reference image for the aorta extraction is the image on which the trachea bifurcates into bronchi, as shown in rendering 520 of FIG. 5A. Voxels in the reference image with intensity values above an aorta threshold value (about 20 HU in CT images) are determined and labeled. The distance from each of these labeled voxels to the nearest non-labeled voxel in the reference image is then determined in a process called hereinafter a distance transformation, and described in more detail below. The voxels farthest from the non-labeled voxels have the greatest distance value. Each labeled voxel that has a local maximum in distance value that is greater than an aorta radius (about 7 mm) is considered as a possible center of the aorta on the reference image. Any 2D object of labeled voxels that includes a possible center voxel is selected as a candidate for the aorta on the reference image.

Roundness.

Roundness of 2D objects is considered in extracting the aorta, using a roundness compact factor (RCF) defined in Equation 1.

$$RCF = 4\pi A/L^2 \qquad (1)$$

Where A is the area of the candidate object and L is the perimeter.

Candidate 2D objects that are considered to be multiple connected anatomical features (such as organs or tissues). [are detached with the algorithm proposed in Subasic M, Loncaric S and Sorantin E., "3D image analysis of abdominal aortic aneurysm," *Proc. SPIE Medical Imaging,* 2002, vol. 4684, pp 1681-1689, hereinafter Subasic, the entire contents of which are hereby incorporated by reference, except where terms are defined to be inconsistent with the use of those terms herein.

Among the aorta candidate objects, the candidate that is in front of the trachea and has the largest product of the area and RCF is taken as the detected ascending aorta. The candidate that is behind the trachea and has the largest product of the area and RCF is taken as the detected descending aorta.

Marker-Controlled Watershed Method.

In an illustrated embodiment, the detected ascending aorta and detected descending aorta are then refined on the aorta reference image with a marker-controlled watershed method. In some embodiments, the aorta candidate is not refined using the marker-controlled watershed method.

The marker-controlled watershed method determines a boundary between tissue characterized by intensity values inside an internal marker and tissue characterized by intensity values along (or outside) an external marker. The method is described in Vincent, L., "Morphological Grayscale Reconstruction in Image Analysis: Applications and Efficient Algorithms," *IEEE Trans. Image Proc.,* 1993, vol. 2, No. 2, pp 176-201 (hereinafter Vincent) the entire contents of which are hereby incorporated by reference, except where terms are defined to be inconsistent with the use of those terms herein. This method is used again in later steps, as described below.

The internal marker is obtained by using a morphologic erosion of the detected ascending/descending aorta with a disk-shaped structure element of 3 pixels radius, thus putting the internal marker about three pixels inside the detected ascending/descending aorta. The external marker is obtained using a morphologic dilation with a disk-shaped structure element of 7 pixels radius, thus putting the external marker about seven pixels outside the detected ascending/descending aorta.

The marker-controlled watershed method is then applied to segment the ascending/descending aorta in the aorta reference image.

Propagation of Boundary to Adjacent Image.

The ascending/descending aorta is determined on adjacent images using a slice-by-slice segmentation method that propagates a boundary on one image to serve as an external marker on the next image. The same method is used in later steps to propagate lymph node boundaries, as described in more detail below. The anatomical object segmentation result on each image, e.g., starting with a reference image, is propagated to the next image in the propagation direction until no anatomical object is identified in the adjacent image. The boundary propagation is done by uniformly extending the anatomical object boundary toward its outside by a distance that based on the slice interval (e.g., axial distance between axially adjacent images).

Figure 10:
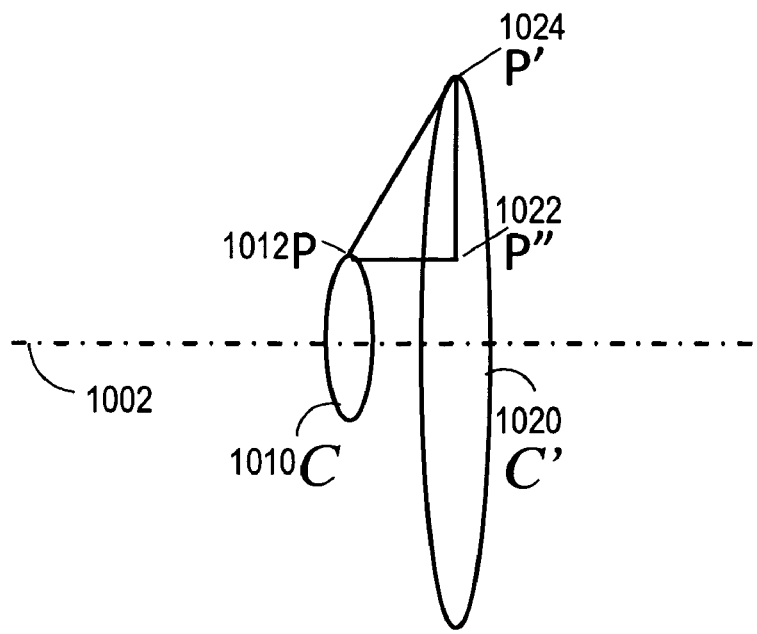
FIG. 10 is a block diagram that illustrates propagation of an edge between adjacent slices of scanned images of a body at a particular time, according to an embodiment.

FIG. 10 is a block diagram that illustrates propagation of an edge between adjacent slices of scanned images of a body at a particular time, according to an embodiment. An axial line segment 1002 passes through a center voxel on a segmented image and a corresponding voxel on the next image in the propagation direction. Closed curve C 1010 is the anatomical object boundary on the currently segmented image and closed curve C' 1020 is the external marker on the adjacent image that should enclose the entire anatomical object on the adjacent image. Point P 1012 is a point on C 1010 and point P' 1024 is its corresponding point on C' 1020. Point P'' 1022 is the point on the adjacent image that has the same transverse plane coordinates as point P. Line segment PP'' indicates the slice interval; and line segment P'P'' indicates an expansion distance. In the illustrated embodiments, the expansion distance P'P'' is chosen to equal twice the slice interval PP''', so that the angle P'P P''' is about 60 degrees.

An internal marker is determined from the geometric center of the external marker and a threshold determined as described in more detail below with reference to FIG. 9A through 9H. The marker-controlled watershed method is then applied on the adjacent image using the internal and external markers to obtain a boundary for the anatomical object on the adjacent image. That boundary is used to define an external marker on the next adjacent image and so on until few or no pixels of the anatomical object are found on an adjacent image.

For segmenting the ascending/descending aorta, the propagation process ceases if the aorta area on a new image increases more than 3 times or decreases to less than 30% of that on the previous image.

Perspective surface rendering 520 of FIG. 5A depicts an example of the extracted aorta, both ascending and descending portions, using this method. Rendering 510 shows the relative positions of the segmented aorta and segmented trachea.

In an illustrated embodiment, the aorta segmentation is carried through the abdomen anatomical domain and to the top of the pelvis anatomical domain.

3.1.3 Automatic Detection of Landmarks-of-Interest in the Abdomen Domain.

In the abdomen anatomical domain, the anatomical landmarks-of-interest includes a collection of abdominal organs that includes a liver, spleen, stomach, kidneys, intestines, inferior vena cava, fat and muscle.

Liver.

For the liver extraction, the lung bottom image is chosen to be a liver reference image. Voxels in the liver reference image that have intensity values above a liver threshold value (about 20 HU in CT images) are determined and labeled. 2D objects of labeled voxels are determined. The distance transformation is applied to the 2D objects to determine the distance from each labeled voxel to the nearest non-labeled voxel. The voxel that has the maximal distance value in the right part of the body is selected as a liver seed point around which a square liver region-of-interest (ROI) is generated. The center of the liver ROI is the liver seed point; and the edge length of the liver ROI is about two thirds of the distance value at the liver seed point. Two threshold values are determined for the intensity values of voxels in the liver ROI.

Dual Threshold Determination.

In general, dual threshold values, $T_{low}$ and $T_{high}$, are determined for a ROI using Equations 2a and 2b.

$$T_{low} = I_{mean} - w_1 * I_{std} \quad (2a)$$

$$T_{high} = I_{mean} + w_2 * I_{std} \quad (2b)$$

Where $I_{mean}$ is the mean of the intensity values in the ROI, $I_{std}$ is the standard deviation of intensity values in the ROI, and $w_1$ and $w_2$ are weighting factors that are determined by experiment to give good segmentation results for a particular purpose.

For segmenting the liver in CT images, $w_1=1.2$ and $w_2=1.2$. Voxels with intensity values in the range from $T_{low}$ to $T_{high}$ are labeled as refined liver voxels and 2D objects of such labeled voxels are determined. The largest such labeled object that includes the liver seed point is considered an approximate 2D segmented liver. New dual thresholds are determined using the approximate 2D liver as the ROI and the same values for $w_1$ and $w_2$. Voxels with intensity values in the new range from $T_{low}$ to $T_{high}$ are labeled as better liver voxels. The same range is used to find connected better liver voxels on adjacent images, until no such voxels are found. The resulting 3D object of final liver voxels is used as the liver extracted from the set of images.

Spleen and Stomach.

For the spleen and stomach extraction, the same voxels in the liver reference image that have intensity values above the liver threshold value and grouped into 2D objects are used, along with the distance transformations. The voxel that has the maximal distance value in the left back part of the body is selected as a spleen seed point. The voxel that has the maximal distance value in the left front part of the body is selected as a stomach seed point. The rest of the processing parallels the liver processing described above.

Kidney.

For the kidney extraction in scanned images, a single, higher threshold is first used to segment the image, because the kidneys have higher intensities than those of the livers on contrast-enhanced images. The threshold level is determined based on the extracted liver using Equation 3 for CT images.

$$T_{kidney} = IL_{mean} + 1.5 * IL_{std} \quad (3)$$

where $IL_{mean}$ is the average intensity of the extracted liver, and $IL_{std}$ is the intensity standard deviation of the extracted liver. The reference image is selected as the middle image in the abdomen anatomical domain, which has an axial position that is a mean axial position of the abdominal domain, where both kidneys are typically found. The left (or right) kidney is the largest object located at the left (or right) side of the spine. The determined largest object on one side is the kidney candidate object and is used to define a new kidney threshold given by $T_{low}$, in Equation 2a, where the largest object is the ROI and the weighting parameter $w_1$ is 1.732. The kidney in the reference image is then obtained by determining voxels with intensity values above the new kidney threshold; labeling 2D objects on the voxels having the intensities higher than the new kidney threshold; and selecting the largest 2D object.

The kidney is tracked on the remaining images with the following slice-by-slice strategy. The new kidney threshold is used to segment 3D objects; and connected components are labeled on each of the 2D images. The tracking is performed in opposite axial directions from the reference image. Along each axial direction, geometric overlap of each of the 2D objects identified on the current image with the kidney segmented on the previous image is tested. If 20% of the object's area overlaps with the kidney on the previous image, the object is considered as part of the kidney on the current image. To protect against including too many voxels in the current image, the kidney segmented on the previous image is expended by 5 voxels and serves as a mask to remove any objects outside the mask on the current image. If the 2D kidney object on the current image is less than 50 voxels in size, the tracking stops.

Intestines.

For extraction of the intestines, regions of air inside the intestines are first detected with an air threshold technique (about −190 HU in CT scans); a voxel with lower intensity indicates air. Higher intensity walls of the intestines are then detected based on the air locations and intensity values. Voxels that fall into about a 5-voxel ring surrounding the air regions and have intensity values larger than a minimum intestine threshold (about 80 HU in CT scans) are used to determine an intestine threshold value. In an illustrated embodiment, a refined intestine threshold is made about equal to the smaller of the mean and the median of the voxels mentioned above. Voxels in the abdomen anatomical domain and in the pelvis anatomical domain, which have intensity values greater than the refined intestine threshold value and are connected to the air regions, are labeled as intestine voxels. Inferior vena cava.

For extraction of the inferior vena cava, a vena cava reference image is selected closer to the bottom of the abdomen domain than to the top (e.g., the axial distance to the bottom lung image is twice the axial distance to the image at the top of the ilium). Voxels in the vena cava reference image that have intensity values above a vena cava threshold value (about 20 HU in CT scans) are determined and labeled. 2D objects of labeled voxels are determined. The distance transformation is applied to the 2D objects to determine the distance from each labeled voxel to the nearest non-labeled voxel. The local maximal points located at the right side of the extracted aorta, which also have a distance less than about 4 centimeters (cm, 1 cm=$10^{-2}$ meters) to the aorta, are selected. This is because the inferior vena cava often runs in parallel with the descending aorta, particularly in a lower body anatomical domain. For each local maximal point, a 2D object that contains the local maximal point is selected as a candidate for the inferior vena cava. Any other objects that are connected to the candidate are detached with the algorithm proposed in Subasic, cited above.

For each object, the RCF is calculated according to Equation 1. Another parameter, called size similarity, SS, is defined by Equation 4.

$$SS=\min(\text{aorta area, object area})/\max(\text{aorta area, object area}) \quad (4)$$

where min and max are two operators that respectively determine the smaller one and the larger one from the data indicated inside the parentheses. Among the objects, the inferior vena cava is the one that has the largest product of SS*RCF. The inferior vena cava on other images is tracked from one image to an adjacent image using the same method as described above for the extraction of the aorta.

Fats and Muscle.

Fats are extracted using an experimentally determined threshold. In an illustrated embodiment a threshold of −30 HU is used for CT images.

For extraction of muscles in abdomen and pelvis, the muscle reference image used is the bottom image in the pelvis. With the bones and fats extracted from the image, the remaining is mostly muscles. Voxels in the muscle reference image that have intensity values above a muscle threshold value (about 20 HU in CT scans) are determined and labeled. 2D objects of labeled voxels are determined. The 2D objects are used as the masks for determination of muscles on adjacent images by applying overlapping tests as described in more detail below with reference to the extractions of the psoas.

3.1.4 Automatic Detection of Landmarks-of-Interest in the Pelvis Domain.

In the pelvis anatomical domain, the anatomical landmarks-of-interest includes the aorta, external arteries and a collection of pelvis organs that includes a bladder, psoas, fat and muscle.

Aorta and External Arteries.

For extraction of the aorta and connected external arteries, a wave propagation technique is used as described in F. K. H. Quek, C. Kirbas, "Vessel extraction in medical images by wave-propagation and trace back", *IEEE Trans. on Med. Img.*, 2001, vol. 20, pp 117-131, the entire contents of which are hereby incorporated by reference, except where terms are defined to be inconsistent with the use of those terms herein. The vena cava reference image is used as the reference image for the extraction of the external arteries. The center of the aorta on the vena cava reference image is chosen as the wave origin for the propagation. Based upon the intensities of the extracted aorta and inferior vena cava and muscle, medium states for the model are determined. Some voxels, which have intensities close to that of the aorta, have faster wave propagation speed and lower medium states. Other voxels have lower speed and higher medium states. The wave propagates as rays that are refracted from the high speeds toward the low speeds. Thus, after the propagation, each voxel in a given intensity range in the image of the pelvis bottom, is traced back to the wave origin. Thus for each voxel, there is a ray path. And for each ray path, a cost is calculated, which is the average of medium states along the ray path. In both left and right sides, the ray path which has the smallest cost is selected as an estimate of the external artery. Thus, two optimized paths are obtained using the wave propagation model, positioning roughly the left and right external arteries. Starting from the reference image to the end of the set of scanned images, voxels are determined in each image, which have intensity values above an artery threshold. The artery threshold is the mean intensity of the extracted inferior vena cava. The 3D objects that connect to the extracted aorta and the optimized paths are considered to be the aorta and the external arteries.

Figure 7:
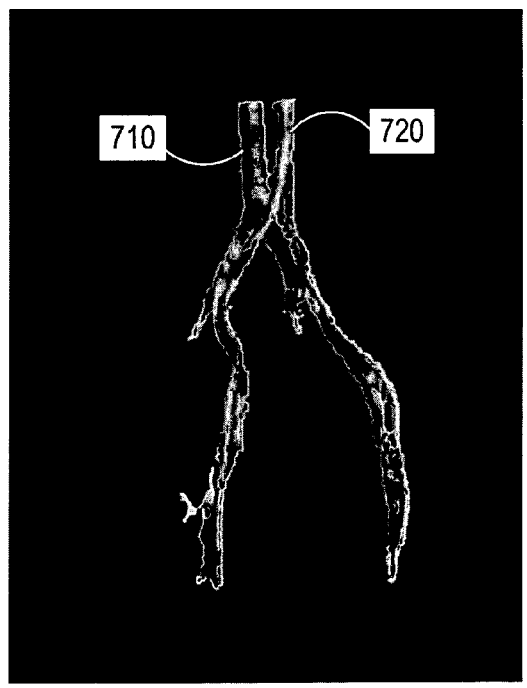
FIG. 7 is a perspective rendering that illustrates major blood vessels extracted from CT imagery, according to an embodiment.

FIG. 7 is a perspective surface rendering that illustrates major blood vessels extracted from CT imagery, according to an embodiment. The rendering includes an aorta and external arteries 710, and a vena cava 720 extracted by the methods described above.

Bladder.

In some embodiments, extraction of the bladder uses a bladder reference image determined by analysis of the bone area profile as shown in FIG. 6, described above. Between the two highest peaks in the pelvis anatomical domain, the scanned image associated with the deepest trough is found; and the bladder reference image at axial position 614 is about halfway between the deepest trough and the right one of the two highest peaks, associated with axial position 616 for the pubis. Voxels in the bladder reference image that have intensity values above a bladder threshold value (about −30 HU in CT scans) are determined and labeled. 2D objects of labeled voxels are determined. The distance transformation is applied to the 2D objects to determine the distance from each labeled voxel to the nearest non-labeled voxel. The voxel with maximum distance, which is also located in the middle part of the image is selected as a bladder seed point. Dual thresholds are estimated using Equations 2a and 2b and a ROI made up of voxels in a square surrounding the bladder seed point with a square side length and weighting factors as described for the extraction of the liver. Voxels in the bladder reference image that have intensity values between the dual thresholds are determined and labeled anew. 2D objects of the new labeled voxels are determined. The distance transformation is applied again to the 2D objects. The new 2D object with the largest diameter located nearest the middle of the image is bladder on the reference image. The voxels in the bladder are then tracked to adjacent images using the same method of extracting and tracking as described above for the kidney.

Determination of the position of the bladder using the bone curves may be affected by other enhanced structures such as the intestines. Thus another method with dual thresholds and no reference image is used for extracting the bladder in some embodiments. Considering that the bladder is the biggest organ containing urine, which has the same intensity in most scanned images as water, the low threshold value is chosen as a water value (about −30 HU in CT scans). To obtain the high threshold value, a histogram of the voxels that have density values between water and a trial threshold (from about −30 HU to about 150 HU in CT images) is calculated. A new high threshold value is determined by choosing the intensity value that corresponds to the highest peak on the histogram. A series of binary images indicating labeled voxels is generated by using the water and high threshold values. Distance transformation is then applied to the binary images. The estimated center of the bladder is determined by taking the voxel position on which the maximum distance value occurs among all images in the set of images.

Psoas.

For the extraction of psoas, the psoas reference image is the top image of the pelvis, including the top of the ilium. On the psoas reference image, the extraction method is the same as that used in the extraction of the aorta. The only difference lies in the selection of two candidates for the psoas. The two candidate objects that are largest in size, located at each side of the spine and possess a compact shape are considered to be the psoas. A two-dimensional Hessian Matrix with small scales (ranging from 9-13 voxels) is then applied to each of the other images in the pelvis to enhance any dot-shaped objects. (See Qiang Li, Shusuke Sone, Kunio Doi, "Selective enhancement filters for nodules, vessels, and airway walls in two- and three-dimensional CT scans", *Med. Phys.* 2003, Vol. 30, No. 8, pp 2040-2051, hereinafter Qiang, the entire contents of which are hereby incorporated by reference, except where the definition of terms conflicts with the definitions used herein.) Voxels in psoas reference image that have intensity values above a psoas threshold value (about 0 HU in CT scans) are determined and labeled. Due to noise, the muscles and other surrounding structures may be divided into separated small objects. A candidate object on an adjacent image is determined to be a part of psoas only when more than 50% of its area geometrically overlaps with the psoas segmented on the previous image. The propagation is performed along one axial direction from the psoas reference image to the bottom of the pelvis domain.

Fats and muscles are extracted as described above for the abdomen anatomical domain. When all these anatomical objects relevant to lymph node location have been extracted, step 222 concludes in method 220, and control passes to step 224.

3.1.5 Automatic Detection of Search Regions Based on Landmarks-of-Interest.

In step 224, the search volumes for lymph nodes, also called the volumes of interest (VOI), are determined based on the extracted anatomic landmarks-of-interest. In the chest anatomical domain, the VOIs are 3 cm thick rings around the aorta and trachea. In the abdomen anatomical domain, the VOIs are the voxels with the already extracted anatomical objects excluded. In the pelvis anatomical domain, the VOIs are 3 cm thick rings around the aorta and external arteries and the groin area with the other extracted anatomical objects excluded.

3.1.6 Automatic Detection of Lymph Tissue Candidate Objects.

In step 226, lymph tissue candidate objects are detected based on multi-resolution Hessian Matrix. On each of the images in the set, six dot-enhancement Hessian matrixes (scales: 9-13 voxels, 13-19 voxels, 19-25 voxels, 25-31 voxels, 31-37 voxels, and 37-43 voxels) are applied to produce six Hessian-transformed images. Voxels in the Hessian-transformed image that have intensity values above a lymph Hessian threshold value (about 0.1 for CT images) are labeled. 2D objects are determined on the image. 2D objects smaller than 9 voxels are then removed. All other 2D objects obtained at different scales are retained and considered as lymph tissue candidate objects.

3.1.7 Automatic Elimination of False-Positive Candidate Objects.

In step 228, false-positive candidates are eliminated based on known properties of lymph nodes. A number of rules are built and parameters are developed to reduce false-positive rate from the detected lymph node candidates.

For example, if a candidate is not in the defined search volumes, or if 5% of its area falls within the other extracted anatomical objects, the candidate is considered as a false-positive and removed from the candidate list.

As another example, if the value of RCF of a 2D candidate is smaller than 0.5, or if a ratio of the maximal diameter to its maximal perpendicular diameter is greater than 3.5, the candidate is considered to be a false-positive node and removed.

In some embodiments, intensity statistics are used to remove false-positive candidates. Statistics of real lymph nodes are studied and their ranges are determined for the scanning device used. These include, but are not limited to, mean intensity, standard deviation in intensity, Skewness and Kurtosis extracted from histogram of intensity gradient in each of multiple directions, and texture features of gray level co-occurrence matrix (GLCM) and gray tone difference matrix (GTDM). Candidates are deleted if any of their features' values falls outside the ranges of these statistics for real lymph nodes.

The following intensity statistical parameters are used in the reduction of the false-positives for CT images.

1] Mean intensity and intensity standard deviation ranges for true positives are (−20 HU to about 80 HU) and (<40 HU), respectively.

2] Skewness and Kurtosis ranges of intensity gradient used for true positive node candidates are (−4.0 to about 2.0) and (−2.0 to about 20.0), respectively. The statistics of the gradient are accumulated in 8 equal directional divisions spanning 0 to 360 degrees.

3] GLCM texture features include Energy, Entropy, Inverse Difference, Maximum Probability, Absolute Value and Correlation. The distances used are 1 and 2 voxels. The angles used are 0°, 45°, 90° and 135°. These features are defined in A. Materka, M. Strzelecki, "Texture Analysis Methods—A Review", Technical University of Lodz, institute of Electronics, COST B11 report, Brussels, 1998 (hereinafter Materka). The features and their ranges used for true positives are Energy (dx=0,dy=2) (<0.06), Correlation (dx=1,dy=1) (>0.4), Maximum probability (dx=0, dy=2) (<0.15), Absolute value (dx=−1,dy=1) (<12), Absolute value (dx=1,dy=1) (<14), Inverse difference (dx=−1, dy=1) (>0.11), Inverse difference (dx=2,dy=0) (>0.06), Inverse difference (dx=0,dy=2) (>0.035), Inverse difference (dx=−2,dy=2) (>0.03) and Inverse difference (dx=2, dy=2) (>0.04).

4] GTDM texture features include Coarseness and Contrast, as described in Materka. The distances used are 1, 2, 3 and 4 voxels. The feature ranges used for true positives are Coarse (width=1) (<0.5), Coarse (width=2) (<0.2), Coarse (width=3) (<0.12), Coarse (width=4) (0.09), Contrast (width=1) (<0.4), Contrast (width=2) (<0.8), Contrast (width=3) (<1.2) and Contrast (width=4) (<1.5)

Figure 8A:
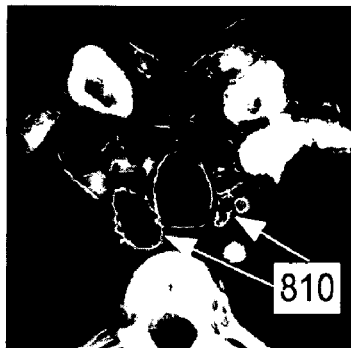
FIGS. 8A through 8C are images that illustrate CT scanned images at three axial locations, respectively, of a chest anatomical domain with boundaries of detected lymph nodes superimposed, according to an embodiment.
Figure 8B:
Figure 8C:
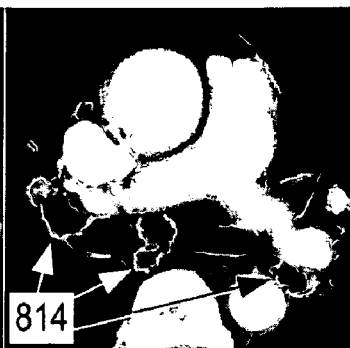

FIGS. 8A through 8C are images that illustrate CT scanned images at three axial locations, respectively, of a chest anatomical domain with boundaries of detected lymph nodes superimposed, according to an embodiment. Automatically detected lymph node boundaries determined without human intervention appear as white closed boundaries 810 in FIG. 8A, boundaries 812 in FIG. 8B, and boundaries 814 in FIG. 8C. These boundaries are quite satisfactory. Similar good results are obtained in the abdomen and pelvis anatomical domains, as illustrated in the next six figures.

Figure 8D:
FIGS. 8D through 8F are images that illustrate CT scanned images at three axial locations, respectively, of an abdomen anatomical domain with boundaries of detected lymph nodes superimposed, according to an embodiment.
Figure 8E:
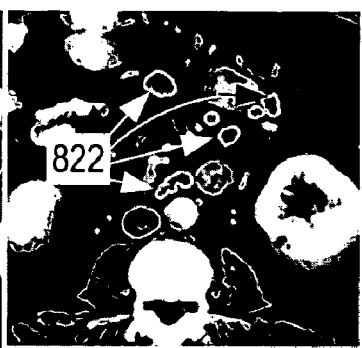
Figure 8F:
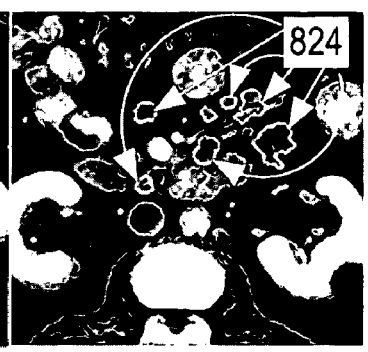

FIGS. 8D through 8F are images that illustrate CT scanned images at three axial locations, respectively, of an abdominal anatomical domain with boundaries of detected lymph nodes superimposed, according to an embodiment. Automatically detected lymph node boundaries determined without human intervention appear as white closed boundaries 820 in FIG. 8D, boundaries 822 in FIG. 8E, and boundaries 824 in FIG. 8F.

Figure 8G:
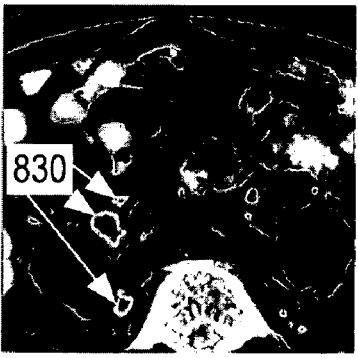
FIGS. 8G through 8I are images that illustrate CT scanned images at three axial locations, respectively, of a pelvis anatomical domain with boundaries of detected lymph nodes superimposed, according to an embodiment.
Figure 8H:
Figure 8I:
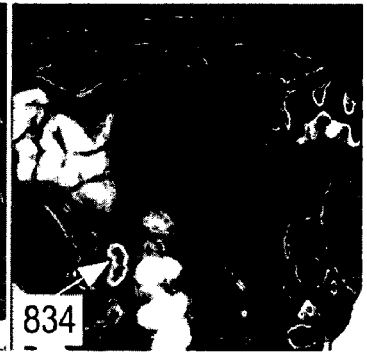

FIGS. 8G through 8I are images that illustrate CT scanned images at three axial locations, respectively, of a pelvis anatomical domain with boundaries of detected lymph nodes superimposed, according to an embodiment. Automatically detected lymph node boundaries determined without human intervention appear as white closed boundaries 830 in FIG. 8G, boundaries 832 in FIG. 8H, and boundaries 834 in FIG. 8I.

3.2 Automatic Segmentation of Lymph Nodes.

FIG. 3 is a flow diagram that illustrates at a high level a method 300 for performing step 206 of the method of FIG. 2A, according to an embodiment. In this method an approximate lymph node boundary in one scanned image is used for an automatic refined segmentation of the lymph node in that image and to propagate the segmentation in adjacent images, without human intervention, based on a marker-controlled watershed method, described above for segmenting the aorta. An example embodiment of method 300 is described for operating on volumetric CT images. For example, this method is used when only a few of all the lymph nodes detected using method 220 are of interest for the diagnosis or treatment of a disease or assessment of the treatment; or the automatic boundaries of those few nodes are to be confirmed.

In step 302, one or more scanned images with a lymph node of interest, taken at a particular time, are received.

In step 304 outline data is received. The outline data indicates a node region of interest (ROI) on one or more scanned images. In some embodiments, the outline data is the boundary of one or more lymph nodes determined automatically, without human intervention, by the method 220, described above. In some embodiments, the outline is provided manually, e.g., by a radiologist drawing a closed curve around a lymph node of particular interest. In some embodiments, the node ROI is generated from the automatically detected node boundary by uniformly extending the automatically detected node boundary, on the image where the node has the maximal area, towards its outside by 5 or 7 voxels. The subsequent segmentation procedures are performed in the ROI. The center of the circle or geometric center of the closed curve is preferably inside the lymph node and is referred to as a lymph seed point hereinafter. Robust determination of internal marker (a region inside the target) and external marker (a region contained within the background) is the key to successful use of the marker-controlled watershed transform in the segmentation of lymph nodes and is the focus of an illustrated embodiment.

In step 306 an internal marker is determined based on the outline data. FIGS. 9A through 9I are images that illustrate images and edges derived from a single CT scanned image and outline data, according to an embodiment. These images illustrate the determination of the internal marker.

FIG. 9A is an image that illustrates the reference image 910 with a node of interest, an initial closed curve 912 enclosing the node ROI, and seed point 914. A median filter of a size of 5×5 voxels is used to reduce noise. An edge detector is then applied. In the illustrated embodiment, a Canny edge detector is used. FIG. 9B is an image that illustrates the reference image 910 with detected edges 920 superimposed. The edge image is then cleaned by removing unwanted edges including any edge that is shorter than 5 pixels in length or has at least one edge that is longer than 5 pixels between the edge and the seed point. FIG. 9C is an image that illustrates the reference image 910 with the remaining edges 930. FIG. 9D is an image that illustrates the reference image 910 with the remaining edges connected with a linear interpolation to form a closed curve 940. In some embodiments, the linear interpolation is performed in polar coordinates with the seed point as the origin and angle as the independent variable.

The area enclosed by the closed curve 940 is then used to identify a rough lymph node candidate. This is achieved by estimating dual threshold values with the pixels in the enclosed area as the ROI, using Equations 2a and 2b, where $w_1=w_2=2.0$. FIG. 9E is the resultant binary image where white voxels have the value of one ("1") and represent the labeled voxels on the reference image with intensity values that fall into the range spanned by the two thresholds. Black voxels have the value of zero ("0") and correspond to the voxels on the reference image with intensity values that fall outside the range spanned by the two thresholds. Connected groups (i.e., geometrically connected non-zero pixels) form 2D objects that are labeled by assigning an identical number to the voxels in each object. The three largest 2D objects 951, 52 and 953 are indicated in FIG. 9E. The object (if there is more than one object) that has the seed point in it, is selected as a lymph node area-of-interest (AOI). Prior to the calculation of the distance map, all other objects are set to zeros and holes in the AOI (i.e., black areas inside the node AOI) are filled to form refined AOI 960 as shown in FIG. 9F.

Under the distance transformation, the Euclidean distance from every non-zero pixel in the AOI to its nearest zero pixel is then calculated to form a distance image as shown in FIG. 9G. The distance values 970 inside the AOI include local maxima at voxels 972 and 974. The distance values 970 are sorted. Starting from the voxel possessing the largest distance value, it is determined whether the distance value is larger than a distance between the voxel and the lymph seed point. If so, a circle centered on this voxel includes the lymph seed point, and this voxel is considered as the center of a circular internal marker. The distance value at this voxel is used as the radius of the circular internal marker. Otherwise, the next voxel with the next largest distance value is examined. This procedure continues until a voxel that satisfies the above criterion is found. The determined internal marker, i.e., the black region 982 inside the lymph node, is shown in FIG. 9H along with the portion 980 of the reference image inside the closed curve 912 of the node ROI.

In step 308, the region outside the node ROI is determined as an external marker, i.e., the black region outside the closed curve 912 as shown in FIG. 9H. These voxels characterize a background outside the node.

In step 310, it is determined if the scan data represents true 3D data with no unsampled gaps between sampled slices, or more traditional scanned images with gaps between the sampled slices. If not true 3D data, then control passes to step 312.

In step 312, 2D marker-controlled watershed method is applied to segment the lymph node on the reference image. In the illustrated embodiments, a gradient image is obtained with the Sobel operator. A grayscale reconstruction algorithm, as described in Vincent, cited above, is used to modify the gradient image to ensure local minima only occur in the region between the two markers. The traditional watershed transform is then applied to the modified gradient image to obtain the lymph node boundary in the region between the two markers. FIG. 9I demonstrates the node segmentation result as boundary 990 on the reference image 910. The boundary 990 is obtained with the marker-controlled watershed algorithm developed in the illustrated embodiment. Control then passes to step 314.

In step 314, the node volume is obtained by propagating segmented edges to adjacent images in a slice-by-slice manner. In one embodiment, the segmented boundary is propagated to the adjacent image and dilated as illustrated above with reference to FIG. 10 to form an external marker for the adjacent image. A seed point is determined for the adjacent image based on the external marker, and an internal marker is derived, as described above for the reference image, with a threshold determined using the currently segmented lymph node intensity and Equation 2a and 2b.

In another embodiment, the segmented lymph mode contour from the current slice is propagated to its adjacent slice by estimating a rough lymph node contour in the adjacent slice using the fast free form deformable (FFD) registration method. (See Weiguo Lu, Ming-Li Chen, Gustavo H Olivera, et al., "Fast free-form deformable registration via calculus of variations", *Phys. Med. Biol.*, 2004, vol. 49, pp. 3067-3087, hereinafter Lu, the entire contents of which are hereby incorporated by reference, except where terms are defined to be inconsistent with the use of those terms herein.) The current slice is registered to the adjacent slice using the FFD, and the resulting transform is used to propagate the boundary from the current slice to the adjacent slice. The transformed boundary is then expanded outward by several voxels to produce the propagated boundary. The propagated boundary is then used to determine the external and internal markers for the refined segmentation of the lymph node in the adjacent slice, as described above.

Control then passes to step 316 to determine if there is another adjacent slice. If so control passes back to step 314. If not, control passes to step 324 to determine the volume of the segmented lymph node. Control then passes to step 208 of method 200 to segment images taken at a different time, if any.

FIGS. 11A through 11G are images that illustrate CT scanned images at seven axial locations, respectively, of an anatomical domain with outline data for CT scanned image 11C superimposed, according to an embodiment. The seven scanned images are 1101, 1102, 1103, 1104, 1105, 1106 and 1107, respectively. On image 1103 depicted in FIG. 11C, an outline 1110 and seed point 1112 are superimposed.

FIGS. 11H through 11N are images that illustrate the same CT scanned images of FIGS. 11A through 11G, respectively, with automatically segmented lymph node edges superimposed, according to an embodiment, using the 2D slice by slice propagation method of step 314. The boundary 1121 is detected in image 1101; boundary 1122 is detected in image 1102; boundary 1123 is detected in image 1103; boundary 1124 is detected in image 1104; boundary 1125 is detected in image 1105; boundary 1126 is detected in image 1106; and boundary 1127 is detected in image 1107. These boundaries are quite satisfactory, as can be seen by comparing to boundaries determined manually by a trained radiologist.

FIGS. 11O through 11U are images that illustrate CT scanned images of FIGS. 11A through 11G, respectively, with manual lymph node edges superimposed. The boundary 1131 is manually drawn in image 1101; boundary 1132 is manually drawn in image 1102; boundary 1133 is manually drawn in image 1103; boundary 1134 is manually drawn in image 1104; boundary 1135 is manually drawn in image 1105; boundary 1136 is manually drawn in image 1106; and, boundary 1137 is manually drawn in image 1107. The boundaries are very similar to the boundaries automatically determined without human intervention and depicted in FIG. 11H through FIG. 11N, respectively TABLE 1 shows summary statistics for the performance of the slice-by-slice segmentation method based on the comparison of the computer segmentation results and the radiologist's manual delineation results. The comparison is quite favorable and on the order of variability among manual results for the same image, while offering the speed and reproducibility of a computer automated method.

TABLE 1 summary statistics for the performance of the slice-by-slice segmentation method.

| Comparison items | Mean | Std dev. | Min. | Median | Max. |
| --- | --- | --- | --- | --- | --- |
| Average distance (mm) | 0.7 | 0.2 | 0.4 | 0.7 | 1.4 |
| Hausdorff distance (mm) | 3.7 | 1.9 | 1.6 | 3.2 | 7.8 |
| Overlap ratio | 83.2% | 4.3% | 72.9% | 83.3% | 93.2% |
| Over-estimated ratio | 13.5% | 7.0% | 0.8% | 13.8% | 32.0% |
| Under-estimated ratio | 5.5% | 3.6% | 0.0% | 4.6% | 14.4% |

If it is determined, in step 310, that the set of scanned images represent true 3D data, then control passes to step 322. A 3D node candidate that approximates the lymph node is obtained to determine an internal and an external marker. In some embodiments step 310 is performed after step 312. With intensities inside the target lymph node segmented on the reference image in step 312 or in outline data received instep 304, dual threshold values are estimated using Equations 2a and 2b with the ROI set to the inside of the segmented node on the reference image. These dual thresholds are then applied to the volumetric images. By labeling voxels in 3D connected groups and selecting the 3D object that has the seed point in it, the lymph node 3D volume-of-interest (VOI) is determined. Prior to the calculation of the distance map, all other non-zero voxels are set to zeros and holes inside the VOI are filled. The Euclidean distance from every voxel in the VOI to its nearest zero voxel is then calculated to form a distance image in a 3D space.

It is recognized that such a 3D VOI may contain the 3D lymph node candidate and possibly other soft-tissue objects with similar intensity values to which the lymph node is attached. In some embodiments, the compact form of most lymph nodes is exploited to detach such non-lymph objects.

A 3D distance analysis algorithm is derived from the 2D distance analysis algorithm of Subasic and Breu H, Gil J, Kirkpatrick D, and Werman M., "Linear Time Euclidean Distance Transform Algorithms," *IEEE Trans. PAMI*, 1995, vol. 17, pp 529-533 (hereinafter Breu) the entire contents of which are hereby incorporated by reference, except where terms are defined to be inconsistent with the use of those terms herein.

Figure 12A:
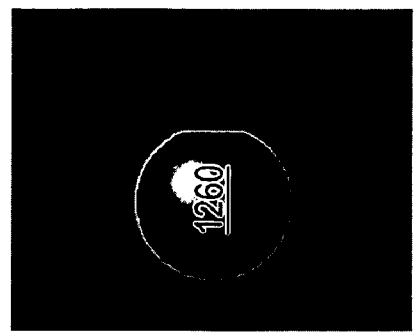
Figure 12B:
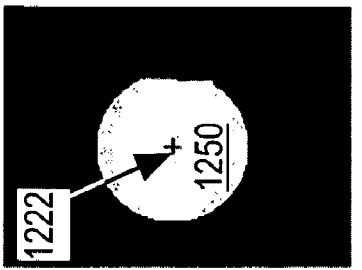
Figure 12C:
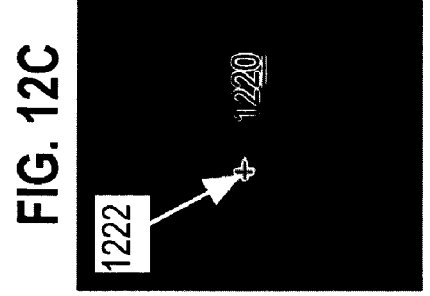
Figure 12D:
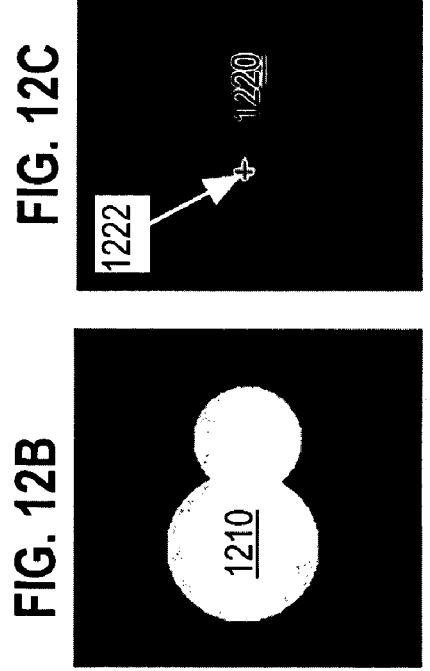
Figure 12E:
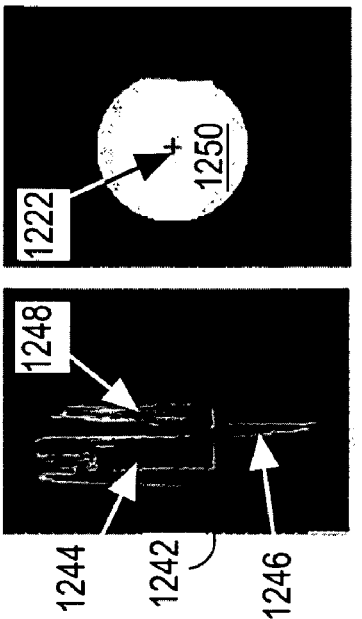
Figure 12F:
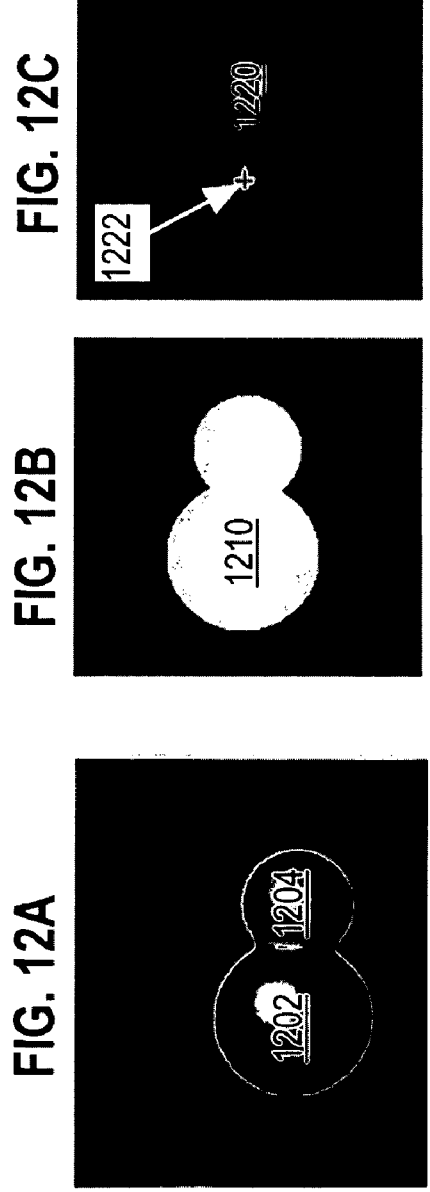
Figure 12G:
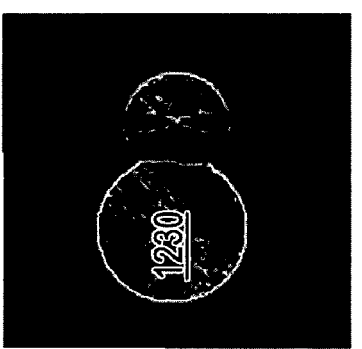

FIGS. 2A through 12G are renderings that illustrate simulated joined anatomical objects before or after detachment, according to an embodiment. The concept of this algorithm is illustrated with two connected spheres. FIG. 12A shows an image of two connected spheres 1202 and 1204 generated by computer. FIG. 12B is a binary image obtained with a thresholding method that shows a single 3D object 1210. To separate the target object (e.g., large sphere 1202) from the connected object (e.g., smaller sphere 1204) that is attached to it, a 3D distance transformation, as describe by Breu, is first applied to the binary image. The result is shown in FIG. 12C as grayscale values 1220 proportional to a distance from a voxel to an edge of the binary object 1210. 3D distance gradient values, derived from the 2D definition, is then calculated based upon the distance image, as shown in FIG. 12D as grayscale values 1230. FIG. 12E renders values 1230 such that the height indicates the magnitude of the distance gradient; and zero is indicated by plane 1242. In FIG. 12E it is evident that at the two sides of the interface between the target object and the connected object, the value of the distance gradient changes from positive 1244 to negative 1246 and then back to positive 1248. The interface between the two objects can thus be identified by the negative values; and the connected object can then be removed from the target object so that the seed point 1222 remains in the target object 1250 and no voxels are included that are separated from the seed voxel by a negative gradient value. The detached target 1250 object is viewed two dimensionally in FIG. 12F and the detached target 1260 object is viewed three dimensionally in FIG. 12G.

Starting with the received lymph node candidate, the internal marker and the external marker are then obtained by using 3D morphologic erosion (i.e., shrinking of the node candidate) and dilation (i.e., expanding of the node candidate), respectively. A sphere-shaped structuring element with a relatively small radius of about 5 voxels is used for the morphologic operators in the illustrated embodiments. A 3D grayscale reconstruction algorithm is then applied to modify the gradient images that are obtained with the Sobel operator to ensure that the local minima only occur between the two 3D markers. The traditional 3D marker-controlled watershed transformation is finally applied to segment the lymph node volume on volumetric CT images.

Control then passes to step 324 to determine the volume of the segmented lymph node.

3.3 Automatic Registration of Image Sets from Different Times.

FIG. 4 is a flow diagram that illustrates at a high level a method 400 for performing two steps of the method of FIG. 2A, according to an embodiment, for the registration step 208 and segmentation step 210 of the lymph nodes, on a second set of scanned images taken at a different time. Method 400 includes steps 401 through 410 for registration and steps 412 through 414 for segmentation. The registration method involves an axial alignment by comparing the shape of the superior lungs between the two sets of scanned images, an in-plane alignment along the x and y directions by translating geometric centers of the two body contours extracted from the two scanned images from the two times, and a non-rigid fast free form deformation (FFD). The segmentation steps include a multi-resolution template matching by an application of parameters concerning similarity of a lymph node between the two set of scanned images at different image resolutions. Preferably, the parameters involve at least node size, shape, intensity distribution and location In step 401, a first set of one or more scanned images and associated lymph node data is received for a particular measurement time. The lymph node data indicates boundaries for one or more target lymph nodes in the first set. In an illustrated embodiment, step 401 includes receiving a set of volumetric CT images with the target lymph nodes segmented automatically as described in method 220 or method 300, or both. For purposes of illustration it is assumed that the first set includes multiple scanned images at corresponding different axial positions.

In step 402, a second set of one or more scanned images is received for a different measurement time. For purposes of illustration it is assumed that the second set includes multiple scanned images at corresponding different axial positions.

In step 404 an axial alignment is determined for an image of the first set and an image of the second set based on lung tissue voxels in the two sets. The lung tissue is extracted from each set using any method known in the art, such as the method of Hu, cited above, to extract lung tissue from CT images. One or more scanned images of the two sets are aligned by comparing the lung shape. In the illustrated embodiments, the lung area curve (LAC) is defined as the distribution of the lung area (in $mm^2$) in the axial direction.

Figure 13:
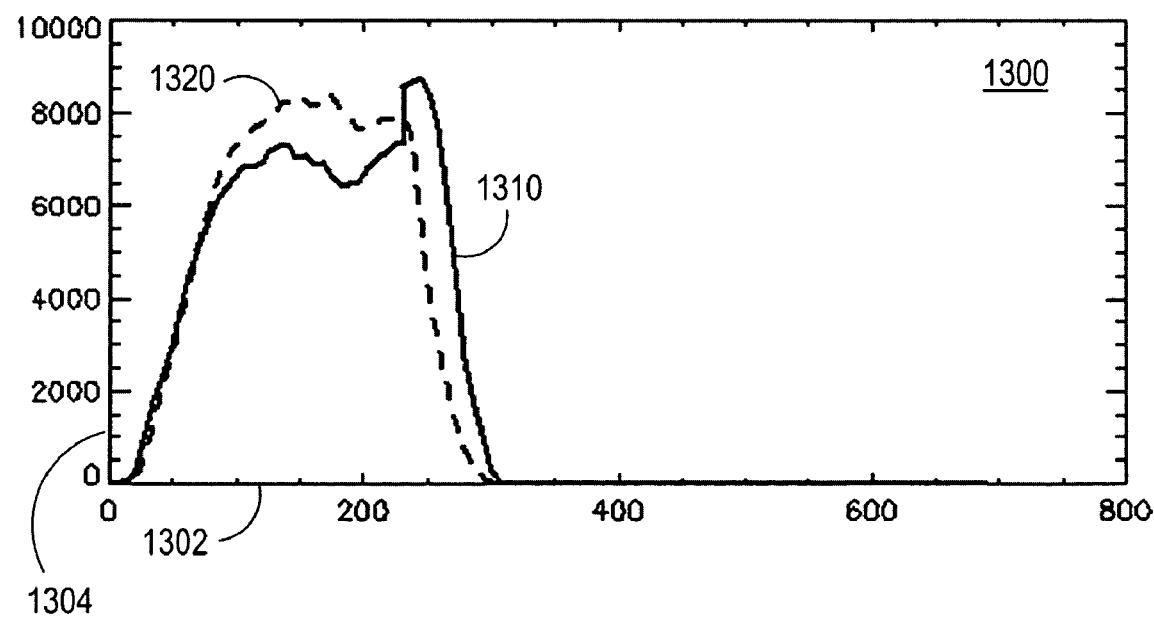
FIG. 13 is a graph that illustrates axial alignment based on lung area profiles derived from CT imagery, according to an embodiment.

FIG. 13 is a graph that illustrates axial alignment based on lung area profiles derived from CT imagery, according to an embodiment. The horizontal axis 1302 is axial position as indicated by scanned image number, increasing from the image closest to the neck toward the image at the bottom of the pelvis. The vertical axis is lung area in square millimeters ($mm^2$). FIG. 13 shows two representative LACs 1310 and 1320 calculated from a patient on two sets of CT images. LAC 1310 indicates the lung shape at the time of measurement of the first set of images with segmented lymph nodes; and LAC 1320 indicates the lung shape in the second set of images from the different measurement time. It is evident that a patient's LACs on the two sets of CT images nearly overlap with each other in the superior lung portion, indicating the similarity of the lung shapes at that anatomic level. By comparing the shape of the superior lungs on the two scans, the two sets of scanned image can be aligned along the axial direction. In order to obtain a reliable result, thick slice images (e.g., 7.5 mm and 5 mm) are linearly interpolated to 1.0 mm slice thickness images prior to the curve comparison.

Let $LAC_B(i)$, $i=1, 2, \ldots, N_B$, be the lung area at the scanning position i in the first set of scanned images (also called baseline images) and $LAC_F(i)$, $i=1, 2, \ldots, N_F$, be the lung area at the scanning position i in the second set of scanned images at a different measurement time (also called follow-on images, although the different time may be before the baseline images in some embodiments), where $N_B$ and $N_F$ are the numbers of the scanned images containing the lungs in the corresponding sets. To calculate a possible position shift between the two sets of scanned images, a subset $[LAC_F(j), LAC_F(k)]$ (j and k are the first and the last image numbers spanning the subset, and j<k) from the second set $LAC_F$ is chosen and dynamically compared with subsets of the same length taken from the first set $LAC_B$. The parameters j and k are obtained using Equation 5, 6 and 7.

$$LAC_F\_MAX = \max_i \{LAC_F(i)\}, (i = 1, 2, \ldots, N_F) \quad (5)$$

$$j = \min\{i \mid LAC_F(i) \geq 0.10 \cdot LAC_F\_MAX, i = 1, 2, \ldots, N_F\} \quad (6)$$

$$k = \min\{i \mid LAC_F(i) \geq 0.25 \cdot LAC_F\_MAX, i = 1, 2, \ldots, N_F\} \quad (7)$$

where $LAC_F\_MAX$ is the global maximum of the lung areas calculated from the second set. From the lung apex to its base, the lung area increases, reaches its global maximum (with some fluctuations), and then decreases. Equations 6 and 7 define the positions j and k in the second set, where the lung area reaches 10% and 25% of the maximal lung area, respectively. The parameters of 10% and 25% were determined experimentally. Equation 8 is then used to determine the start image (position) p in the first set, from where the best matching (i.e., the smallest difference) between the subset of the first set [$LAC_B(p)$, $LAC_B(p+(k-j))$] and the subset of the second set [$LAC_F(j)$, $LAC_F(k)$] occurs.

$$p = \operatorname*{argmin}_{t \in [1, N_B-(k-j)]} \left\{ \sum_{i=j}^{k} (LAC_F(i) - LAC_B(t+i-j))^2 \right\} \quad (8)$$

The difference (i.e., shift) between the axial position p and j can then be used to align the two sets in the axial direction. For example, if an image of the first set is scanned at a position i, its corresponding position in the second set is found at the position i+(j−p). The axial position information of an image can be obtained from a DICOM header stored with standard medical image data.

In step 406, a subset of scanned images in the first set that encompasses a lymph node of interest is determined, and the corresponding subset in the second set is determined based on the axial alignment determined in step 404. In the illustrated embodiments, a lymph node subset is defined as the contiguous scanned images containing the lymph node and several more scanned images at each side of the lymph node. The further registration of only the lymph node subsets can help increase the algorithm's accuracy and reduce computation.

In step 408 cross sectional alignment of the lymph node subsets (i.e., in the transverse plane) is determined based on body contours. Transverse plane alignment starts with extractions of the body surfaces from the subset of the two sets of scans. These are done by using a threshold method (body threshold value=−724 HU in CT images) to distinguish voxels outside the body from those inside. The boundary of the voxels above and below this body threshold is the body surface. The 3D geometric centers of the two surfaces are then calculated and compared. Should the two centers not coincide, the two sub-volumes are aligned along the x and y directions so that there is no displacement between the two centers.

In step 410 a non-rigid, fast free form deformation (FFD) method is applied, as described in Lu, cited above, to further register the subsets from the two sets. The registration algorithm allows some automated matching of lymph nodes between the two sets of scans.

FIG. 14A is an image that illustrates a CT scanned image 1410 from a particular time with a detected boundary 1412 of a lymph node superimposed, according to an embodiment. The boundary 1412 is obtained from the lymph node data associated with the image 1410 and receive during step 401.

FIG. 14B is an image that illustrates a corresponding CT scanned image 1420 from a different time with superimposed, the boundary of FIG. 14A deformed based on registration of the corresponding images, according to an embodiment. The deformed boundary 1422 results from the FFD registration. As can be seen, the deformed lymph node boundary 1422 cannot be directly taken as the segmentation result for the scan of the second set. The discrepancy is due to possible tumor change over time and/or registration error. However, the deformed boundary serves as an initial boundary for a subsequent, refined segmentation in the image of the second set. FIG. 14C is an image that illustrates the corresponding CT scanned image 1420 of FIG. 14B with a newly determined lymph node boundary 1432, according to an embodiment. The boundary 1432 is formed by refining the initial boundary 1422, as described in more detail below.

FIG. 15A is an image that illustrates a different CT scanned image 1510 from a particular time with a detected boundary 1512 of a lymph node superimposed, according to an embodiment. FIG. 15B is an image that illustrates a corresponding CT scanned image 1520 from a different time with superimposed, the boundary of FIG. 15A deformed to boundary 1522 based on FFD registration of the corresponding images, according to an embodiment. The actual lymph node 1530 in image 1520 is distinctly apart from the deformed boundary 1522. FIG. 15B shows a serious mismatching of lymph node by FFD registration of the lymph node boundary from the segmented image. The mismatching here means that the deformed lymph node volume does not geometrically overlap with the corresponding node on the follow-up images of the second set.

3.4 Automatic Segmentation of Lymph Nodes at Different Time.

Automated segmentation of images in the second set from a different measurement time is performed in steps 412, 413 and 414.

3.4.1 Templates for Refined Segmentation.

In step 412, a multi-resolution template matching method is applied to correct the mismatching from FFD deformed boundaries of the segmented image. The principle behind this new matching technique lies in the similarity of lymph node intensities on the image from the first and second sets. In various embodiments, such similarity includes, but is not limited to, the location, size, shape and intensity distribution of the voxels that represent the lymph node. Utilizing the lymph node segmented on the baseline images of the first set, multi-resolution templates can be built. These templates are then used to match the corresponding lymph node on the follow-up images of the second set.

For the segmented lymph node in the image of the first set, a cuboid that minimally encloses the node is extracted and serves as the original template. Multiple other templates are obtained for different scales by super-sampling or down-sampling this original template. Each template represents a growing or shrinking lymph node to be matched to the images of the second set at the different time. In the illustrated embodiment, the sampling scale factor ranges from 0.6 to 1.5 with an interval of 0.1 to produce 10 templates. Tri-linear intensity interpolation is used to resample the templates. For each template, the intensities of the lymph node voxels remain unchanged, whereas the intensity of the background voxels (i.e., the voxels outside the node in the template) is assigned a value of zero (0). These 10 templates are then used as multi-resolution templates for the subsequent node matching.

FIGS. 16A through 16C are images that illustrate templates at three different scales based on a single lymph node, according to an embodiment.

A search region in the image of the second set is determined. Preliminary results showed that the maximal displacement of the lymph nodes between the two scans after the FFD registration was about 2 cm, 2 cm and 1.5 cm along the x, y and axial (z) directions, respectively. Thus a cubic search region was chosen. The center of the search region locates at the center of the deformed lymph node and extends about 7 cm along the x and y directions and about 5 cm along the axial direction (z axis).

FIGS. 6D through 16F are images that illustrate images and edges derived from a single CT scanned image at the different time and the templates of FIGS. 6A through 16C, according to an embodiment. FIG. 16D shows one image of the cubic search region.

To further reduce computation, the voxels in the search region that are unlikely to be part of the lymph node to be matched are excluded from the subsequent matching procedure. Based on the assumption that a lymph node should have a similar intensity range in the two scans, the intensity distribution of the lymph node in the image of the first set is used to determine the node candidate voxels in the follow-up scan. Dual thresholds are determined using Equations 2a and 2b for a ROI that comprises the segmentd lymph node in the image from the first set, and weighting factors $w_1$ and $w_2$ both equal to 2.5. In the search region, only the voxels whose intensities fall into the intensity range between the two thresholds are considered as node candidate voxels. FIG. 16D shows the detected node candidate areas 1640 in one image from the second set at the different time.

For a given resolution, the center of the template is placed at each of the lymph node candidate voxels in the search region in the image at the different time. All voxels in the image at the second time, which are also inside the cuboid covered by the template that is centered at a node candidate voxel form a candidate node window. At each node candidate voxel, a number of similarity features defined below (Equations 9-13) are calculated from the template and the candidate node window. By combining these features using Equation 14, a single similarity value is obtained for each candidate voxel. Mapping similarity values of all node candidate voxels generates an output response image of the template-matching at the given resolution. This process repeats itself for each of the template resolutions. The resultant output at all resolution levels is then combined to enhance the lymph node matching. This is achieved by a nonlinear combination of the outputs of the multi-resolution template-matching, e.g., by taking the maximum response among the multiple responses at each voxel as the final output. FIG. 16E shows one image of the response of the multi-resolution template-matching. A voxel 1652 with relatively low similarity is indicated, as are voxels 1654, 1656 with relatively high similarity.

After obtaining the location of one voxel 1656 having the maximum value in FIG. 16E, the lymph node can be localized. FIG. 16F is the segmentation result using the corrected location. If the location of the voxel having the maximum response value does not correspond to the lymph node location, the location of the voxel having the second maximum value is taken and tested. This continues until a satisfactory segmentation result is achieved as examined by comparing the segmented lymph node using the deformed lymph node at the corrected location as an initiation to the baseline lymph node. Alternatively, in some embodiments, local maxima are detected by the technique described in Zhao B, Gamsu G, Ginsberg M S, Jiang L, Schwartz L H., "Automatic detection of small lung nodules on CT utilizing a local density maximum algorithm," *J. Applied Clinical Medical Physics*, 2003, vol. 4, No. 3, pp 248-260. For each local maximum location, using the deformed lymph node as an initiation, a segmented lymph node, i.e., a node candidate, is obtained. By comparing the similarity between each of the node candidates with the baseline lymph node, the lymph node in the follow-up image can be determined, which is the one that has the highest similarity to the baseline lymph node.

As mentioned previously, a number of similarity features can be extracted from the template and the candidate node window at each candidate node voxel for a given resolution. Let a be the lymph node region in the template taken from the image of the first set and a' the background outside the node and inside the template. The values of $a_i$ (i=0, . . . n−1) and $a_i'$ (i=0, . . . $n_{temp}$−n) are intensity values of the $i^{th}$ voxels in the regions a and a', respectively, where n is the voxel number of the lymph node and $n_{temp}$ is the total voxel number of the template. Likewise, geometrically, b=a and b'=a' in the candidate node window. The values of $b_i$(i=0, . . . n−1) and $b_i'$ (i=0, . . . $n_{temp}$−n) are the intensity values of the $i^{th}$ voxels in the regions b and b' in the candidate node window in image of the second set, respectively.

The first feature is the cross-correlation coefficient (CC) defined in Equation 9 and Equation 10. CC is a similarity measure based on the intensity distributions of the two regions (a and b) to be compared.

$$CC = \frac{\sum_{i=0}^{n-1}(a_i - m_a)(b_i - m_b)}{\sqrt{\sum_{i=0}^{n-1}(a_i - m_a)^2}\sqrt{\sum_{i=0}^{n-1}(b_i - m_b)^2}} \tag{9}$$

where $m_a$ and $m_b$ are the average intensities of the regions a and b, respectively.

$$m_a = \frac{1}{n}\sum_{i=0}^{n-1} a_i, m_b = \frac{1}{n}\sum_{i=0}^{n-1} b_i \tag{10}$$

CC value ranges from −1 to +1. A high positive value indicates a high correlation, whereas a high negative value specifies a high inverse correlation.

The second intensity-based similarity between the lymph node in first set and the node candidate in the second set is a new measure, SI, defined in Equation 11.

$$SI = e^{\frac{-|m_a - m_b|^2}{2 * Istd^2}} \tag{11}$$

where $I_{std}$ is the intensity standard deviation of intensity values in the region a. SI values range from 0 to 1. If $m_a = m_b$, then SI=1; otherwise, SI<1. The larger the difference between the two regions' (a and b) average intensity, the smaller the value of SI.

The third intensity-based similarity, SG, is new and indicates the match of the node size as given by Equation 12.

$$SG = \frac{\min(|m_a - m_{a'}|, |m_b - m_{b'}|)}{\max(|m_a - m_{a'}|, |m_b - m_{b'}|)} \tag{12}$$

where $m_{a'}$ and $m_{b'}$ are the averages of intensities in the two background regions a' and b', respectively. The values of SG range from 0 to 1. The closer the size of the scaled lymph node matches the node in the follow-up images, the larger the value of SG. For an extreme example, if the scaled node b is part of the template covered area that has homogenous intensity distribution in the images of the second set, i.e., $m_b = m_{b'}$, then in this unmatched situation, SG=0.

To reduce the possibility of including a non-node area as a node, a new distance constraint feature, SD, is defined by Equation 13a and 13b.

$$SD = \exp\{(dd - Tdist)^2 / (2Tdist^2)\} \quad \text{for } dd > Tdist \quad (13a)$$
$$= 1.0 \quad \text{for } dd < Tdist \quad (13b)$$

where dd is the distance of the candidate voxel at which the template is centered to the center of the deformed lymph node. Tdist (=1.5 cm) is a constant. The search region is defined relatively larger so as not to miss the node. This feature gives a larger value to a mis-matched node that has a smaller registration error The above defined features are combined in Equation 14.

$$S_{combined} = w_1*(CC+1)/2 + w_2*SI + w_3*SG + w_4*SD \quad (14)$$

where $w_1, w_2, w_3$ and $w_4$ are weighting parameters. Currently, these parameters are all set equal to 1. Preferred values are readily determined by one of ordinary skill through experimentation. In the equation, we use (CC+1)/2 instead of CC so that the value is normalized to the range [0,1].

The result is the location of a voxel at the center of the lymph node in one or more images of the second set, at the second measurement time. This voxel is taken as a lymph seed value in the next steps.

3.4.1 Marker-Controlled Watershed Segmentation of Images at Different Time.

In step 413, internal and external markers are determined for the scanned image from the second set based on the lymph seed voxel, the lymph node data in the first set, and the registered, deformed lymph node data in the second set.

Based on expecting that the intensities of a lymph node on the two subsets of the sets of images should not differ significantly, the intensity distribution of the identified lymph node on the subset of the first set of images, along with the registered, deformed node contours on the subset of the second set of images, are used to help recognize the corresponding lymph node on the subset of the second set of images.

Dual thresholds are determined using Equation 2a and 2b for a ROI encompassing the segmented lymph node in the subset of the first set and $w_1 = w_2 = 2.5$. By applying these two thresholds to the images of the subset of the second set, a set of binary volumetric images is obtained. In the binary images, the voxels with the value of one (1) represent the voxels whose intensities fall into the range spanned by the two thresholds, whereas the voxels with the value of zero (0) correspond to the voxels whose intensities are outside the range spanned by the two thresholds. To determine the lymph node in the subset of the second set of images, connected voxel groups are analyzed among the voxels having the value of 1 on the follow-up binary images of the subset of the second set. The object having the largest volume intersected by the deformed lymph node contours in 3D space is identified as the lymph node volume-of-interest (VOI) in the subset of the second set of images.

It is assumed for purposes of illustration that the target lymph node on the images of the first set is O. After registration, O is deformed to O' on the images of the second set. The intersection area of the lymph node VOI and O' in every image is calculated. The different time node reference image, i.e., the first image of the second set in which the segmentation starts, is the image that possesses the maximal intersection area.

Holes in the intersection area are filled. This region is then morphologically eroded on each image of the subset of the second set by a disk-shaped structuring element with a radius of 3 pixels, and the result serves as the internal markers.

It is assumed that the shape of a lymph node does not change considerably between the first set and the second set at the different measurement time. The lymph node boundary on the reference image of the first set is used to determine the external marker. This is done by translating the boundary from the subset of the first set (without any change in shape) to a place on the corresponding reference image in the second set where the boundary's geometric center coincides with that of the intersection region extracted to determine the internal marker. The translated boundary is then dilated to fully enclose the intersection region and the minimal distance between the two boundaries (i.e., the translated lymph node boundary and a boundary of the intersection region) is greater than a predefined value (e.g., 7 voxels). The region outside the dilated boundary defines the external marker.

Once the internal and external markers are obtained, the marker-controlled watershed transformation is applied to the reference image. Likewise, to obtain the lymph node volume, the segmentation algorithm is implemented in a slice-by-slice manner or a true 3-D manner, in various embodiments, as described above. FIG. 14C shows a segmentation boundary 1432 of a lymph node an image of the second set, using the slice-by-slice propagation.

4.0 Implementation Mechanisms—Hardware Overview

Figure 17:
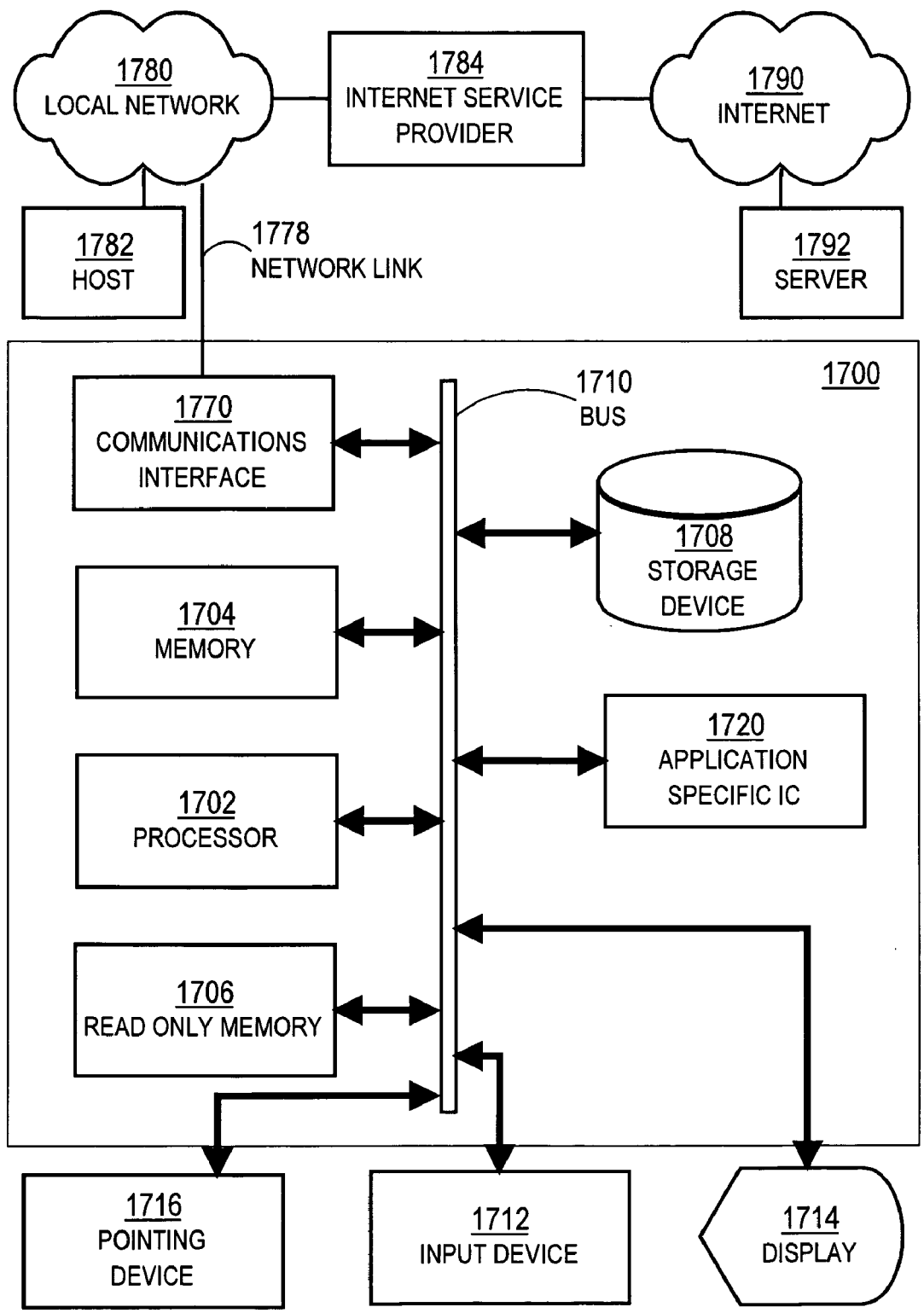
FIG. 17 illustrates a computer system upon which an embodiment may be implemented.

FIG. 17 illustrates a computer system 1700 upon which an embodiment may be implemented. Computer system 1700 includes a communication mechanism such as a bus 1710 for passing information between other internal and external components of the computer system 1700. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 1710 includes many parallel conductors of information so that information is transferred quickly among devices coupled to the bus 1710. One or more processors 1702 for processing information are coupled with the bus 1710. A processor 1702 performs a set of operations on information. The set of operations include bringing information in from the bus 1710 and placing information on the bus 1710. The set of operations also typically include comparing two or more units of information, shifting positions of units of information, and combining two or more units of information, such as by addition or multiplication. A sequence of operations to be executed by the processor 1702 constitute computer instructions.

Computer system 1700 also includes a memory 1704 coupled to bus 1710. The memory 1704, such as a random access memory (RAM) or other dynamic storage device, stores information including computer instructions. Dynamic memory allows information stored therein to be changed by the computer system 1700. RAM allows a unit of information stored at a location called a memory address to be stored and retrieved independently of information at neighboring addresses. The memory 1704 is also used by the processor 1702 to store temporary values during execution of computer instructions. The computer system 1700 also includes a read only memory (ROM) 1706 or other static storage device coupled to the bus 1710 for storing static information, including instructions, that is not changed by the computer system 1700. Also coupled to bus 1710 is a non-volatile (persistent) storage device 1708, such as a magnetic disk or optical disk, for storing information, including instructions, that persists even when the computer system 1700 is turned off or otherwise loses power.

Information, including instructions, is provided to the bus 1710 for use by the processor from an external input device 1712, such as a keyboard containing alphanumeric keys operated by a human user, or a sensor. A sensor detects conditions in its vicinity and transforms those detections into signals compatible with the signals used to represent information in computer system 1700. Other external devices coupled to bus 1710, used primarily for interacting with humans, include a display device 1714, such as a cathode ray tube (CRT) or a liquid crystal display (LCD), for presenting images, and a pointing device 1716, such as a mouse or a trackball or cursor direction keys, for controlling a position of a small cursor image presented on the display 1714 and issuing commands associated with graphical elements presented on the display 1714.

In the illustrated embodiment, special purpose hardware, such as an application specific integrated circuit (IC) 1720, is coupled to bus 1710. The special purpose hardware is configured to perform operations not performed by processor 1702 quickly enough for special purposes. Examples of application specific ICs include graphics accelerator cards for generating images for display 1714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware. Logic encoded in one or more tangible media includes one or both of computer instructions and special purpose hardware Computer system 1700 also includes one or more instances of a communications interface 1770 coupled to bus 1710. Communication interface 1770 provides a two-way communication coupling to a variety of external devices that operate with their own processors, such as printers, scanners and external disks. In general the coupling is with a network link 1778 that is connected to a local network 1780 to which a variety of external devices with their own processors are connected. For example, communication interface 1770 may be a parallel port or a serial port or a universal serial bus (USB) port on a personal computer. In some embodiments, communications interface 1770 is an integrated services digital network (ISDN) card or a digital subscriber line (DSL) card or a telephone modem that provides an information communication connection to a corresponding type of telephone line. In some embodiments, a communication interface 1770 is a cable modem that converts signals on bus 1710 into signals for a communication connection over a coaxial cable or into optical signals for a communication connection over a fiber optic cable. As another example, communications interface 1770 may be a local area network (LAN) card to provide a data communication connection to a compatible LAN, such as Ethernet. Wireless links may also be implemented. For wireless links, the communications interface 1770 sends and receives electrical, acoustic or electromagnetic signals, including infrared and optical signals, that carry information streams, such as digital data.

The term computer-readable medium is used herein to refer to any medium that participates in providing information to processor 1702, including instructions for execution. Such a medium may take many forms, including, but not limited to, non-volatile media, volatile media and transmission media. Non-volatile media include, for example, optical or magnetic disks, such as storage device 1708. Volatile media include, for example, dynamic memory 1704. Transmission media include, for example, coaxial cables, copper wire, fiber optic cables, and carrier waves that travel through space without wires or cables, such as acoustic waves and electromagnetic waves, including radio, optical and infrared waves. Signals include man-made variations in amplitude, frequency, phase, polarization or other physical properties of carrier waves.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 1778 typically provides information communication using transmission media through one or more networks to other devices that use or process the information. For example, network link 1778 may provide a connection through local network 1780 to a host computer 1782 or to equipment 1784 operated by an Internet Service Provider (ISP). ISP equipment 1784 in turn provides data communication services through the public, world-wide packet-switching communication network of networks now commonly referred to as the Internet 1790. A computer called a server 1792 connected to the Internet provides a service in response to information received over the Internet. For example, server 1792 provides information representing video data for presentation at display 1714.

The disclosure is related to the use of computer system 1700 for implementing the techniques described herein. According to one embodiment, those techniques are performed by computer system 1700 in response to processor 1702 executing one or more sequences of one or more instructions contained in memory 1704. Such instructions, also called software and program code, may be read into memory 1704 from another computer-readable medium such as storage device 1708 or network link 1778. Execution of the sequences of instructions contained in memory 1704 causes processor 1702 to perform the method steps described herein. In alternative embodiments, hardware, such as application specific integrated circuit 1720, may be used in place of or in combination with software to implement an embodiment. Thus, embodiments are not limited to any specific combination of hardware and software, unless otherwise explicitly stated.

The signals transmitted over network link 1778 and other networks through communications interface 1770, carry information to and from computer system 1700. Computer system 1700 can send and receive information, including program code, through the networks 1780, 1790 among others, through network link 1778 and communications interface 1770. In an example using the Internet 1790, a server 1792 transmits program code for a particular application, requested by a message sent from computer 1700, through Internet 1790, ISP equipment 1784, local network 1780 and communications interface 1770. The received code may be executed by processor 1702 as it is received, or may be stored in storage device 1708 or other non-volatile storage for later execution, or both. In this manner, computer system 1700 may obtain application program code in the form of signals on a carrier wave.

Various forms of computer readable media may be involved in carrying one or more sequence of instructions or data or both to processor 1702 for execution. For example, instructions and data may initially be carried on a magnetic disk of a remote computer such as host 1782. The remote computer loads the instructions and data into its dynamic memory and sends the instructions and data over a telephone line using a modem. A modem local to the computer system 1700 receives the instructions and data on a telephone line and uses an infra-red transmitter to convert the instructions and data to a signal on an infra-red carrier wave serving as the network link 1778. An infrared detector serving as communications interface 1770 receives the instructions and data carried in the infrared signal and places information representing the instructions and data onto bus 1710. Bus 1710 carries the information to memory 1704 from which processor 1702 retrieves and executes the instructions using some of the data sent with the instructions. The instructions and data received in memory 1704 may optionally be stored on storage device 1708, either before or after execution by the processor 1702.

5.0 Extensions and Alternatives

In the foregoing specification, specific embodiments are described. It will, however, be evident that various modifications and changes may be made thereto without departing from the broader spirit and scope of the disclosure. The specification and drawings are, accordingly, to be regarded in an illustrative rather than a restrictive sense.

What is claimed is:

1. A method comprising automatically detecting a lymph node in a computer tomography X-ray image of internal tissues of a body without human intervention based on applying a dot-enhancement Hessian matrix to voxels in the computer tomography X-ray image.

2. The method as recited in claim 1, further comprising:
receiving a single set of a plurality of computer tomography X-ray images representing corresponding different slices of the body between a neck of the body and a bottom of a pelvis of the body; and
determining a subset of the plurality of the computer tomography X-ray images wherein the subset of the computer tomography X-ray images belongs to one anatomical domain of a plurality of anatomical domains between the neck and the bottom of the pelvis.

3. The method as recited in claim 2, wherein:
the method further comprises determining voxels in the subset associated with an anatomical object that is not a lymph node and which is associated with the anatomical domain; and
automatically detecting the lymph node comprises determining voxels in a search region of a particular image of the subset in a particular spatial relationship outside the voxels associated with the anatomical object.

4. The method as recited in claim 3, wherein:
applying the dot-enhancement Hessian matrix further comprises applying dot-enhancement Hessian matrixes at a plurality of scales to the voxels in the search region to produce a corresponding plurality of transformed images; and
automatically detecting the lymph node further comprises:
determining a set of one or more candidate nodes on the transformed images, wherein each candidate node includes voxels with values above a lymph threshold value which form a contiguous region of more than a particular number of voxels; and
selecting one candidate node of the set as the lymph node.

5. The method as recited in claim 4, wherein selecting one candidate node of the set further comprises:
determining whether a candidate node of the set is a false positive based on known statistics of lymph nodes; and
if the candidate node is a false positive, then removing the candidate node from the set before selecting the one candidate node of the set as the lymph node.

6. A method for segmenting a lymph node comprising the steps of:
receiving a single set of one or more computer tomography X-ray images representing internal tissues of a body at a particular time;
receiving outline data that indicates a region of interest that encloses voxels that represent a lymph node, wherein the region of interest is in the single set of one or more computer tomography X-ray images; and
automatically, without human intervention, segmenting the single set of one or more computer tomography X-ray images to identify a lymph node boundary between voxels that represent the lymph node and voxels that do not, based at least in part on applying a marker-controlled watershed algorithm.

7. The method as recited in claim 6, wherein automatically segmenting the single set of one or more computer tomography X-ray images further comprises:
determining an external marker on a first image in the single set based on the outline data; and
determining an internal marker on the first image based on a geometric center of the outline data; and
wherein applying a marker-controlled watershed algorithm further comprises applying a marker-controlled watershed algorithm that uses the external marker and the internal marker to determine the lymph node boundary on the first image.

8. The method as recited in claim 7, wherein:
the outline data is determined automatically, without human intervention; and
determining an external marker based on the outline data further comprises determining an external marker edge that is several voxels outside the region of interest indicated in the outline data.

9. The method as recited in claim 7, wherein:
the outline data indicates a two-dimensional region of interest in a single reference image of the single set of one or more computer tomography X-ray images; and
determining the internal marker further comprises:
determining an initial set of lymph node voxels based on an upper lymph threshold and a lower lymph threshold;
selecting as a center of the internal marker a voxel in the initial set of lymph node voxels, which voxel is farther from a closest edge of the initial set of lymph node voxels than from the geometric center of the outline data and farther from the closest edge than any other voxel; and
selecting as a radius of the internal marker a distance from the voxel selected as a center to the closest edge of the initial set of lymph node voxels.

10. The method as recited in claim 9, wherein determining the internal marker further comprises:
determining a closed curve based on edges detected inside the region of interest; and determining the upper lymph threshold and the lower lymph threshold based on a mean and standard deviation of the intensity values for voxels inside the closed curve.

11. The method as recited in claim 6, wherein automatically segmenting the single set of one or more computer tomography X-ray images further comprises:
propagating a lymph node boundary from one computer tomography X-ray image to an external marker in an adjacent image in the single set of one or more computer tomography X-ray images;
determining an internal marker inside the external marker based on a geometric center of the propagated external marker in the adjacent image; and
applying a marker-controlled watershed algorithm that uses the external marker and the internal marker to determine a lymph node boundary on the adjacent image.

12. The method as recited in claim 11, wherein propagating the lymph node boundary to the adjacent image further comprises determining the external marker that is outside the lymph node boundary on the one computer tomography X-ray image by a distance that is based on a thickness associated with a single computer tomography X-ray image of a particular scanning device that produced the single set of one or more computer tomography X-ray images.

13. The method as recited in claim 11, wherein propagating the lymph node boundary to the adjacent image further comprises determining a closed curve in the adjacent image based on deforming the lymph node boundary according to a deformation transform determined using a deformable registration method to fit the one computer tomography X-ray image to the adjacent image.

14. The method as recited in claim 7, wherein:
the outline data indicates a three-dimensional region of interest in the set of one or more reference images;
automatically segmenting the set of one or more computer tomography X-ray images further comprises determining an initial set of lymph node voxels based on an upper lymph threshold and a lower lymph threshold;
determining an internal marker comprises eroding several outermost voxels from the initial set of lymph node voxels; and
determining an external marker comprises adding several voxels outward from the initial set of lymph node voxels.

15. The method as recited in claim 14, wherein determining the initial set of lymph node voxels further comprises:
determining a preliminary set of lymph node voxels based on the upper lymph threshold and the lower lymph threshold;
determining a gradient of three dimensional distance from a voxel in the preliminary set to an edge of the preliminary set for every voxel in the preliminary set; and
including voxels of the preliminary set in the initial set based on the gradients of three dimensional distance.

16. A method for segmenting a lymph node at a different time comprising the steps of:
receiving a first computer tomography X-ray image representing internal tissues of a body at a particular time;
receiving lymph node data that indicates a first set of voxels that represent tissue within a particular lymph node in the first computer tomography X-ray image;
receiving a plurality of computer tomography X-ray images representing internal tissues of the same body at a different time; and
segmenting automatically, without human intervention, a second computer tomography X-ray image from the plurality of computer tomography X-ray images at the different time based on the lymph node data, by applying a marker-controlled watershed algorithm to identify in the second computer tomography X-ray image a second set of voxels that represent tissue within a lymph node that corresponds to the particular lymph node at the different time.

17. The method as recited in claim 16, wherein:
receiving the first computer tomography X-ray image further comprises receiving a particular plurality of computer tomography X-ray images representing internal tissues of the body at the particular time;
receiving lymph node data further comprises receiving lymph node data that indicates a first set of voxels that represent tissue within the particular lymph node in a first subset of the particular plurality of scanned images at the particular time, which first subset includes the first computer tomography X-ray image;
the method further comprises determining a second subset of images from the plurality of computer tomography X-ray images at the different time based on the lymph node data, which second subset includes the particular lymph node at the different time.

18. The method as recited in claim 16, further comprising aligning a geometric center of a body surface in the second computer tomography X-ray image with a geometric center of a body surface in the first computer tomography X-ray image, whereby the first computer tomography X-ray image is aligned with the second scanned image in plane.

19. The method as recited in claim 17, further comprising aligning along an axial direction of the body, the plurality of computer tomography X-ray images at the different time to the particular plurality of computer tomography X-ray images at the particular time based on similarity of a lung object in both pluralities of computer tomography X-ray images.

20. The method as recited in claim 16, wherein segmenting the second computer tomography X-ray image further comprises:
registering the first computer tomography X-ray image to the second computer tomography X-ray image using non-rigid fast free form deformation (FFD) algorithm;
determining a search region in the second computer tomography X-ray image based on a deformed boundary that indicates a location of the first set of voxels that represent tissue within the particular lymph node in the first computer tomography X-ray image after registering to the second computer tomography X-ray image; and
determining an initial set of lymph node voxels in the search region with intensity values that fall between an upper lymph threshold and a lower lymph threshold based on values of the first set of voxels.

21. The method as recited in claim 20, wherein segmenting the second computer tomography X-ray image further comprises:
determining candidate lymph node voxels that correspond to the particular lymph node in the plurality of computer tomography X-ray images at the different time based on the deformed boundary and the initial set of lymph node voxels;
determining an internal marker by eroding the candidate voxels about several voxels inside the candidate voxels; and
determining an external marker by expanding the deformed boundary without changing shape to be several voxels outside the candidate voxels; and
wherein applying a marker-controlled watershed algorithm further comprises applying a marker-controlled watershed algorithm that uses the external marker and the internal marker to determine the lymph node boundary at the different time.

22. A computer-readable medium carrying one or more sequences of instructions, wherein execution of the one or more sequences of instructions by one or more processors causes the one or more processors to perform the steps of:
  receiving a set of one or more computer tomography X-ray images representing internal tissues of a body at a particular time;
  receiving outline data that indicates a region of interest that encloses voxels that represent a lymph node, wherein the region of interest is in the set of one or more computer tomography X-ray images; and
  automatically, without human intervention, segmenting the set of one or more computer tomography X-ray images to identify a lymph node boundary between voxels that represent the lymph node and voxels that do not, based at least in part on applying a marker-controlled watershed algorithm.

23. An apparatus comprising logic encoded in one or more tangible media, which, when executed, is operable for:
  receiving a set of one or more computer tomography X-ray images representing internal tissues of a body at a particular time;
  receiving outline data that indicates a region of interest that encloses voxels that represent a lymph node, wherein the region of interest is in the set of one or more computer tomography X-ray images; and
  automatically, without human intervention, segmenting the set of one or more computer tomography X-ray images to identify a lymph node boundary between voxels that represent the lymph node and voxels that do not, based at least in part on applying a marker-controlled watershed algorithm.

24. An apparatus comprising:
  means for receiving a set of one or more computer tomography X-ray images representing internal tissues of a body at a particular time;
  means for receiving outline data that indicates a region of interest that encloses voxels that represent a lymph node, wherein the region of interest is in the set of one or more computer tomography X-ray images; and
  means for automatically, without human intervention, segmenting the set of one or more computer tomography X-ray images to identify a lymph node boundary between voxels that represent the lymph node and voxels that do not, based at least in part on applying a marker-controlled watershed algorithm.

25. A method as recited in claim 3, wherein the anatomical domain is selected from a group of distinct anatomical domains comprising a chest domain, an abdomen domain and a pelvis domain.

26. A method as recited in claim 25, wherein determining voxels in the subset associated with the anatomical object further comprises:
  determining voxels that belong to one or more organs selected from a group of organs for the anatomical domain; and
  removing from the subset the voxels that belong to the one or more organs for the anatomical domain.

27. A method as recited in claim 26, wherein:
  the group of organs for the chest domain comprises an aorta and a trachea;
  the group of organs for the abdomen domain comprises a liver, a spleen, a stomach, a kidney, an intestine, an inferior vena cava, a fat tissue and a muscle tissue; and
  the group of organs for the pelvis domain comprises an aorta, an external artery a bladder, a psoas, a fat tissue and a muscle tissue.

* * * * *